(12) United States Patent
Rao et al.

(10) Patent No.: US 7,303,904 B2
(45) Date of Patent: Dec. 4, 2007

(54) STABLE GENE VARIANTS OF LIPASES

(75) Inventors: Nalam Madhusudhana Rao, Andhra Pradesh (IN); Priyamvada Acharya, Andhra Pradesh (IN)

(73) Assignee: Council of Scientific & Industrial Research, New Dehli (IN)

( * ) Notice: Subject to any disclaimer, the term of this patent is extended or adjusted under 35 U.S.C. 154(b) by 430 days.

(21) Appl. No.: 10/768,951

(22) Filed: Jan. 29, 2004

(65) Prior Publication Data
US 2005/0196834 A1    Sep. 8, 2005

(30) Foreign Application Priority Data
Jan. 30, 2003    (IN) ................ 075/DEL/2003

(51) Int. Cl.
*C12N 9/20*    (2006.01)
*C12N 1/20*    (2006.01)
*C12N 15/00*    (2006.01)
*C07H 21/04*    (2006.01)

(52) U.S. Cl. ............... 435/198; 435/252.3; 435/320.2; 536/23.2

(58) Field of Classification Search ........... 435/198, 435/252.3, 320.1; 536/23.2
See application file for complete search history.

*Primary Examiner*—Tekchand Saidha
(74) *Attorney, Agent, or Firm*—John P. White; Cooper & Dunham LLP

(57) ABSTRACT

The present invention relates to the generation and production of novel thermostable, organic solvent stable and pH tolerant lipase gene variants. The invention also relates to methods of selecting lipase variants for high temperatures and for their purification.

25 Claims, 9 Drawing Sheets

Figure 1:
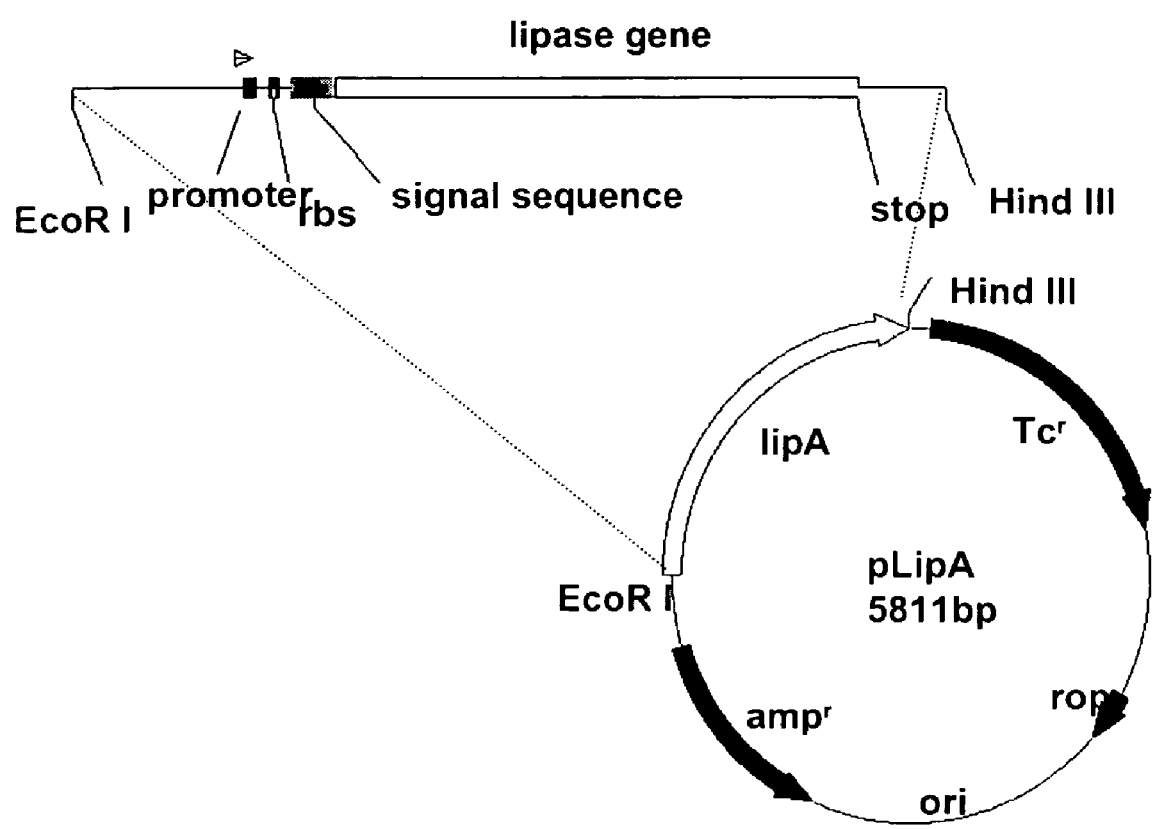

The residual activity of the proteins wt (O), SEQ ID No. 2 (▲),SEQ ID No. 3 (◆),SEQ ID No. 4(□),SEQ ID No. 5 (●),SEQ ID No. 6(■) plotted against the time of exposure at 55 °C, pH 7.

STABLE GENE VARIANTS OF LIPASES

TECHNICAL FIELD

The present invention relates to the generation and production of novel thermostable, organic solvent stable and pH tolerant lipase gene variants. The invention also relates to methods of selecting lipase variants for high temperatures and for their purification.

BACKGROUND AND PRIOR ARTS

Enzymes are the workhorses of a cell that affect virtually every biological process that characterizes a living organism. They catalyze chemical reactions with remarkable specificity and rate enhancements. The awesome catalytic power and versatility of enzymes has long been recognized and enzymes have proved to be very useful outside the living system as well. Enzymes today have widespread application in industry and are seen as environment friendly alternatives to chemical reagents because enzymatic reactions require milder conditions and tend to be cleaner with lesser byproduct and waste generation. Enzymes are being used in numerous new applications in the food, feed, agriculture, paper, leather, and textiles industries, resulting in significant cost reductions and environment-friendly operations.

Enzymes have evolved to function best under the physiological conditions of the parent organism. In vitro applications often call upon enzymes to work under non-physiological conditions or to perform functions they have not evolved for. For example, enzymes may have to catalyze reactions involving novel substrates; they may have to work under extreme conditions of salt, temperature, pH etc., or in the presence of potentially inhibiting or denaturing chemicals. Such applications have brought to light the severe disabilities of enzymes to function as industrial catalysts. In order to extract optimum performance from enzymes in the test-tube and in industrial reactors, these biocatalysts need to be tailored to suit specific applications.

The commercial success of these enzymes can be attributed to their ease of use. In addition to functioning at high temperatures, thermostable enzymes generally posses an increased shelf life which markedly improves handling conditions. If enzymes are to play a significant role in large scale processing of chemicals, they must be able to endure the harsh conditions associated with these processes. Thermostable enzymes are easier to handle, last longer, and given the proper immobilization support should be reusable for multiple applications.

In obtaining thermostable enzymes the conventional approach is to screen the microbial collections collected from extremephillic environments (Karsheroff and Ladenstein, 2001). The promising candidate enzymes are further investigated for suitability for a specific process. For example, for applications requiring thermostable or salt stable enzymes, enzymes from thermophilic or halophilic organisms were used, respectively.

However, such an approach severely restricted the use of enzymes because enzymes for all applications cannot be found in nature. There may not be a natural enzyme for many kinds of transformations. Moreover, enzyme usage is often restricted by undesirable properties of enzymes like product inhibition, low stability etc. Very often an enzyme is required to have a combination of several properties that may be impossible to find in a natural enzyme. Another approach to obtain thermostable enzymes is based on the current knowledge on the protein structures (crystal structures) of homologous enzymes from mesophiles and thermophiles (Kumar et al, 2000; Lehmann et al, 1998). Such comparisons yielded information on the probable interactions that enhance thermostability. Using such information efforts were made to incorporate these changes in mesophilic enzymes to improve their thermostability. Such approaches have not been very successful since interactions that improve thermostability in a protein are many and each protein acquires, over evolutionary times, those interactions that are best suited for its sequence and the mileu in which it functions. Though structural determinants of protein stability have been objects of numerous studies on model proteins, no universal stabilization mechanism has yet been found (Jaenicke and Bohm, 1998). The most obvious conclusion that can be drawn from the literature is that different proteins have adapted to different thermal environments by a variety of evolutionary devices. The lack of understanding of the structural features leading to protein thermostability has been partly due to a scarcity of data because experimental studies comparing homologous proteins from psychrophilic, mesophilic and thermophilic organisms have been limited to only a few proteins. Moreover, inability to form definite rules for improving protein thermostability is due to the large number and complexity of possible contributing factors (Jaenicke and Bohm, 1998; Vogt et al. 1997a; Vogt et al., 1997b; Ladenstein and Antranikain, 1998). Based on comparisons between mesophiles and thermophiles, the main mechanisms responsible for increased thermostability have been identified as increase in the number of hydrogen bonds and salt bridges, increased core hydrophobicity, better packing efficiency, α-helix and loop stabilization and resistance to covalent destruction. Often it becomes difficult to delineate protein interactions that contribute to thermostability from other selection pressures such as salt, pH etc.

Other strategies adapted to increase the thermostability was based on the observation that immobilized enzymes acquire thermostability to some extent (Reetz et al., 1995). Hence, several solid supports were tried to immobilize proteins. And also recent observations made with enzymes in organic solvents indicated that in organic solvents enzymes acquire thermostability (Plou and Ballesteros, 1999). The advent of recombinant DNA techniques has greatly facilitated protein engineering by allowing facile mutagenesis and production of proteins.

The term protein thermostability refers to the preservation of the unique chemical and spatial structure of a polypeptide chain under extremes of temperature conditions (Jaenicke and Bohm, 1998). In general, the higher the temperature to which the enzyme is exposed, the shorter the half-life of the enzyme (i.e., the shorter the enzyme retains its activity). Similarly, the greater levels of organic solvent to which said enzymes are exposed, the shorter the half-life of the enzyme. The phrase "catalytic activity" or simply "activity," means an increase in the k.sub.cat or a decrease in the K.sub.M for a given substrate, reflected in an increase in the k.sub.catt/K.sub.M ratio. The structural basis of protein thermostability has been an actively pursued area of research for at least two decades (Argos et al., 1979). However, enzymes lifted out of the context of living organisms do not always function as well as they do in their natural milieu. For example, they have optimum activity at the physiological temperature of the organism and tend to denature at higher temperatures leading to drop in activity. Thermostable enzymes are important as they can be used at high temperatures and harsher conditions required in industrial contexts. Also they generally have higher storage stabilities and bring down costs by obliviating the need for low temperature storage and decreasing the loss due to denaturation on storage and handling. Moreover reactions carried out at higher temperatures generally proceed at higher rates further bringing down operation times.

In view of the environmental safety reasons, there is a constant pressure to reduce the use of environmentally polluting processes in industry. Enzymes are increasingly used to replace chemical processes in leather, food, and pharmaceutical industries. Comparison of protein structures from extremeophiles demonstrated that protein structural plasticity is enormous and is resident in the primary structure. This lent considerable support to strategies that alter the primary structure of the proteins at the genetic level and screen for the variants with special properties such as thermostability. The tremendous success in handling the genes and developing protocols to alter it at will, has allowed to evolve proteins with special functions. The strategy relies in generating variation in gene sequences by molecular biology methods and screening the variants by expressing them and screening the mutant population (Arnold, 1999; Stemmer, 1994; Ostermeier et al., 1999). The screening protocols are based on the property of interest, e.g., activity at high temperature or activity in the presence of organic solvents. The present invention encompasses methods for generating variation in gene sequences, protocols for screening the enzymes with higher thermostability and also protocols for sequencing and expression.

Lipases (triacylglycerol acylhydrolases, E.C. 3.1.1.3) are water-soluble enzymes that catalyze the hydrolysis of ester bonds in triacylglycerols and often also exhibit phospholipase, cutinase and amidase activities (Woolley and Petersen, 1994). They are used for the production of detergents, pharmaceuticals, perfumes, flavour enhancers and texturising agents in consmetic products. Lipases are crucial for the production of a wide variety of foods, especially for products from milk, fat and oil. Lipases are ubiquitous enzymes of considerable physiological significance and industrial potential. Lipases catalyze the hydrolysis of triacylglycerols to glycerol and free fatty acids. In contrast to esterases, lipases are activated only when adsorbed to an oil-water interface and do not hydrolyze dissolved substrates in the bulk fluid. A true lipase will split emulsified esters of glycerine and long-chain fatty acids such as triolein and tripalmitin. Lipases are serine hydrolases. Commercially useful lipases are usually obtained from microorganisms that produce a wide variety of extracellular lipases (Jaeger et al., 1999). Many lipases are active in organic solvents where they catalyze a number of useful reactions including esterification transesterification, regioselective acylation of glycols and menthols, and synthesis of peptides and other chemicals. An increasing number of lipases with suitable properties are becoming available and efforts are underway to commercialize biotransformation and syntheses based on lipases (Schmid and Verger, 1998). Enzyme sales for use in washing powders still remain the single biggest market for industrial enzymes. The major commercial application for hydrolytic lipases is their use in laundry detergents. Detergent enzymes make up nearly 32% of the total lipase sales. Lipase for use in detergents needs to be thermostable and remain active in the alkaline environment of a typical machine wash. An estimated 1000 tons of lipases are added to approximately 13 billion tons of detergents produced each year Because of their ability to hydrolyzes fats, lipases find a major use as additives in industrial laundry and household detergents. Detergent lipases are especially selected to meet the following requirements: (1) a low substrate specificity, i.e., an ability to hydrolyze fats of various compositions; (2) ability to withstand relatively harsh washing conditions (pH 10-11, ~60° C.); (3) ability to withstand damaging surfactants and enzymes [e.g., linear alkyl benzene sulfonates (LAS) and proteases], which are important ingredients of many detergent formulations. Lipases with the desired properties are obtained through a combination of continuous screening (Jaeger and Reez, 1998; Wang et al.; Rubin and Dennis, 1997) and protein engineering (Kazlauskas and Bornscheuer, 1998). In 1994, Novo Nordisk introduced the first commercial recombinant lipase 'Lipolase,' which originated from the fungus *Thermomyces lanuginosus* and was expressed in *Aspergillus oryzae*. In 1995, two bacterial lipases were introduced—'Lumafast' from *Pseudomonas mendocina* and 'Lipomax' from *P. alcaligenes*—by Genencor International (Jaeger et al., 1999al). According to a report an alkaline lipase, produced by *P. alcaligenes* M-1, which was well suited to removing fatty stains under conditions of a modern machine wash. The patent literature contains examples of many microbial lipases that are said to be suitable for use in detergents (Gerritse et al., 1998).

Lipase-producing microorganisms include bacteria, fungi, yeasts, and actinomyces. *Bacillus subtilis* is a Gram-positive, aerobic, spore-forming bacterium that has generated substantial commercial interest because of its highly efficient protein secretion system Though extracellular lipolytic activity of *B. subtlis* was observed as early as in 1979 (Bycroft and Byng, 1992), molecular research started in 1992 when a lipase gene, lipA, was cloned and sequenced (Dartois et al., 1992). Subsequently the lipase was overexpressed, purified and characterized (Leuisse et al., 1993). Later, a second gene, lipB, was found that is 68% identical with lipA at the nucleic acid level (Eggert et al., 2000). This gene has been cloned and the protein overexpressed, purified and characterized.

The *Bacillus subtilis* lipase with a molecular weight of 19,348 Da is one of the smallest lipases known. It is one of the few lipases that do not show the interfacial activation in the presence of oil-water interfaces. LipA is very tolerant to basic pH and has its optimum activity at pH10. It hydrolyses the sn-1 and sn-3 glycerol esters with both short and long chain fatty acids, showing optimum activity with C8 fatty acid chains.

Bacterial lipases are classified into eight families according to their sequence similarities, conserved sequence motifs and biological properties (Arpigny and Jaeger, 1999). The true lipases are classified in family I which contains six subfamilies. *Bacillus* lipases have been placed in subfamilies 4 and 5. In these two subfamilies alanine replaces the first glycine residue in the conserved G-X-S-X-G pentapeptide around the active site serine residue. Subfamily 4 consists of only three members, LipA and LipB from *B. subtilis* and a lipase from *Bacillus pumilis*, which share 74-77% sequence identity. These are the smallest lipases known and show very little sequence similarity (~15%) with the other, much larger, *Bacillus* lipases that constitute subfamily 5.

The crystal structure of the *B. subtilis* lipase LipA reveals a globular protein with dimensions of 35×36×42 (Pouderoyen et al., 2001). The structure shows a compact domain that consists of six β-strands in a parallel β-sheet, surrounded by α-helices. There are two α-helices on one side of the α/β sheet and three on the other side. The fold of the *B. subtilis* lipase resembles that of the core of the α/β hydrolase fold enzymes. The *B. subtilis* lipase lacks the first two strands of the canonical α/β hydrolase fold and the helix αD is replaced by a small 310 helix. The helix αE is exceptionally small, with only one helical turn, and several α-helices start or terminate with 310 helical turns. Due to these structural features, its small size and absence of a lid domain, the *B. subtilis* lipase is considered a minimal α/β hydrolase fold enzyme.

OBJECTS OF THE INVENTION

The main object of the present invention relates to novel thermostable, organic solvent stable and pH tolerant lipase gene variants.

Another object of the present invention relates to an expression system comprising of novel thermostable, organic solvent stable and pH tolerant lipase gene variants.

Yet another object of present invention relates to a method of preparing an expression system, said system comprising of novel thermostable, organic solvent stable and pH tolerant lipase gene variants.

One more object of the present invention relates to the gene variants wherein the gene have inherent ability to withstand high pH in the range of 10 to 11; ability to withstand damaging surfactants and enzymes comprising groups of linear alkyl benzene sulfonates, proteases and compounds thereof.

Another object of the present invention relates to the gene variants wherein gene variants are useful as stain remover in household detergents and laundry industry.

Yet another object of the present invention relates to the gene variants wherein the gene variants have extremely high specific activity.

BRIEF DESCRIPTION OF ACCOMPANYING FIGURES/DRAWINGS

FIG. 1: The lipA gene pBR 322. The lipA gene containing the entire lipase gene sequence along with the signal sequence, promoter and the ribosome binding sequence was shown.

Figure 2:
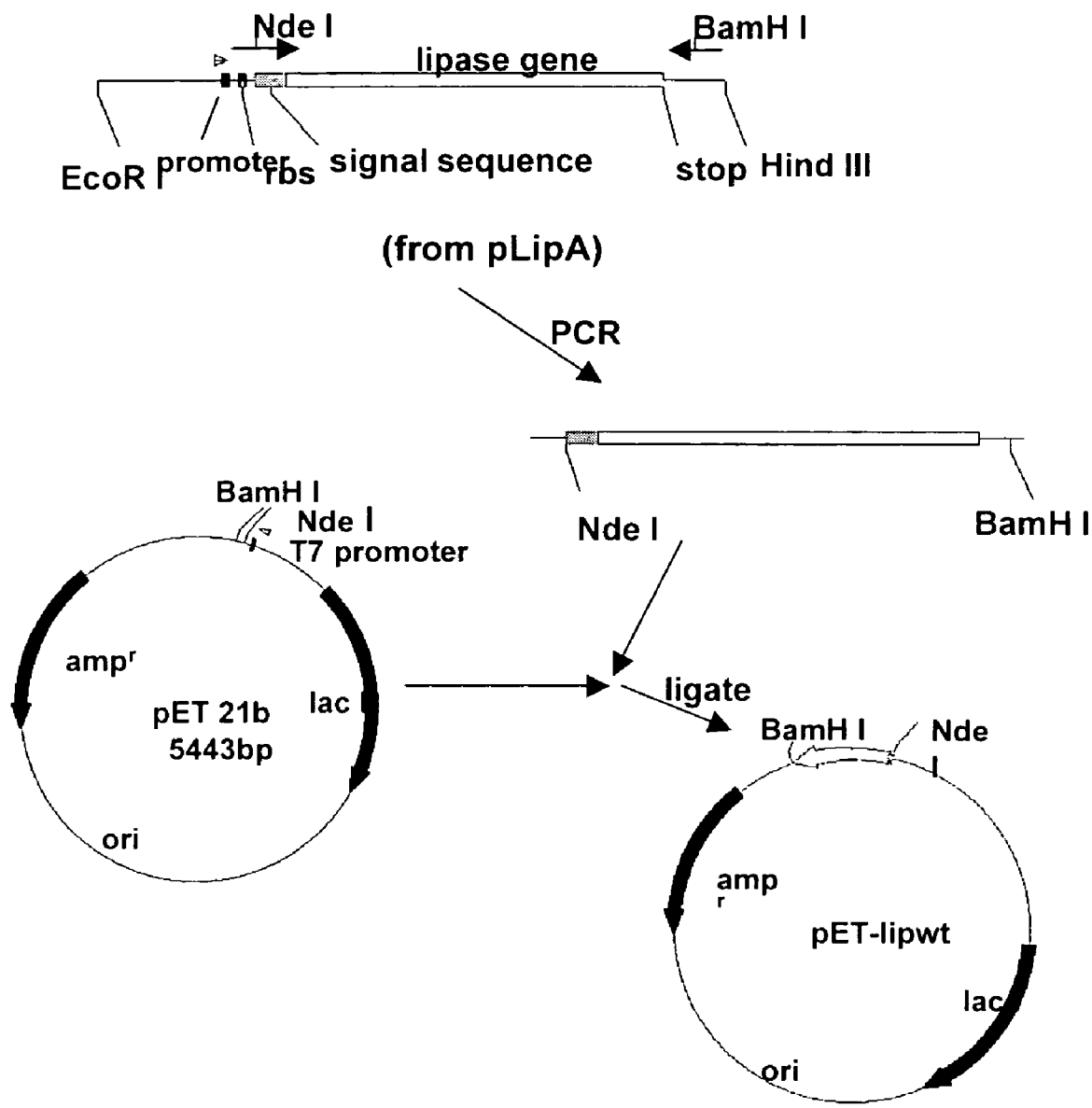

FIG. 2: Subcloning of lipA with the signal sequence into pET21b. The lip A gene along with the signal sequence was amplified using the ForI and RevI primers and then was inserted into the pET21b resulting in pEt-lipwt. The ForI and RevI primers were designed to introduce NdeI and BamHI sites into the LipA gene.

Figure 3:
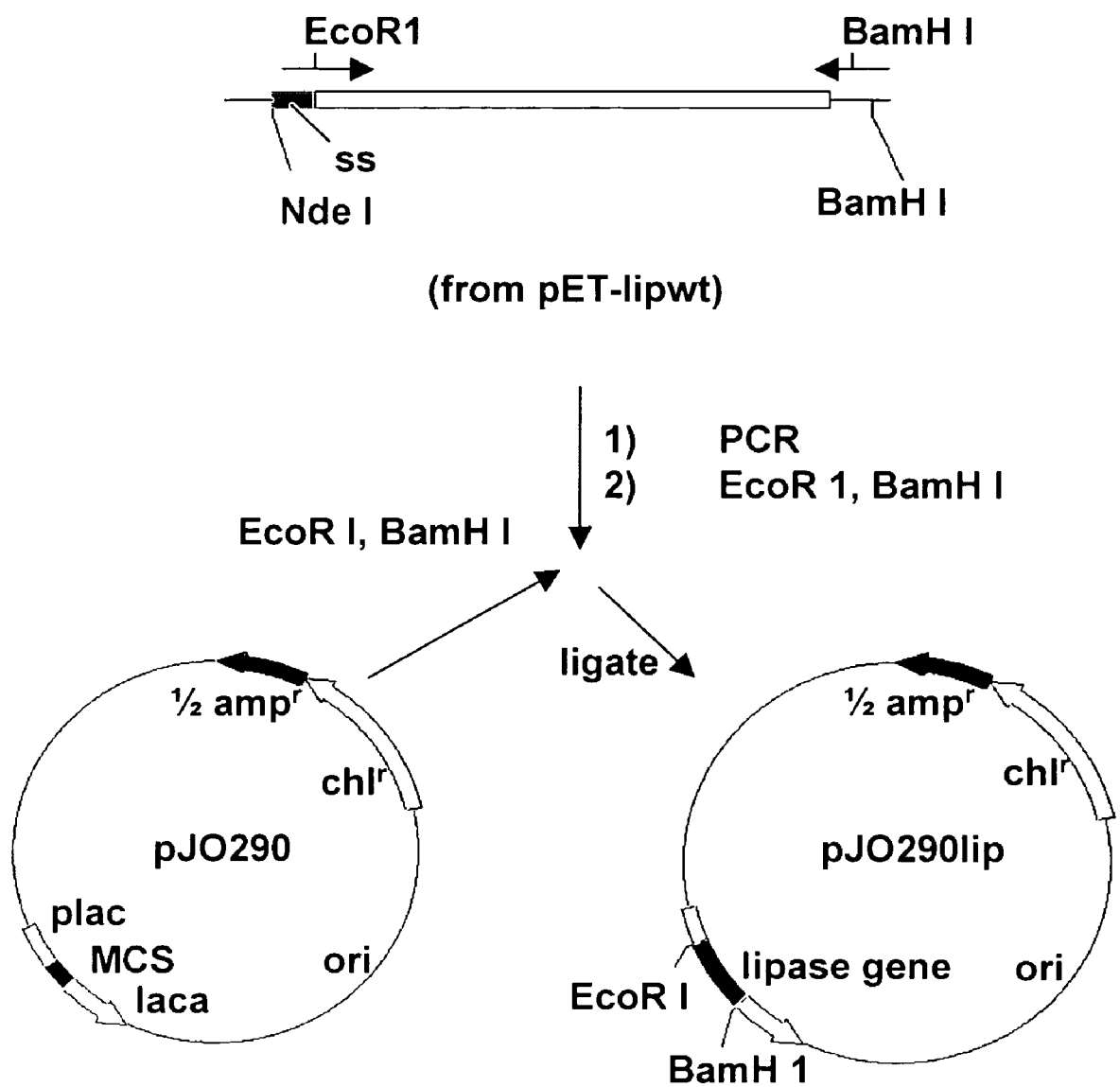

FIG. 3: Subcloning of lipA without signal sequence into pJO290. The lipA gene present in the pET-lipwt was amplified using the PrEcoRI and PRBamHI primers designed specifically to introduce EcoRI and BamHI sites into the amplified products. The amplified product was cut using EcoRI and BamHI and then inserted into pJO290 vector which was similarly cut.

Figure 4:
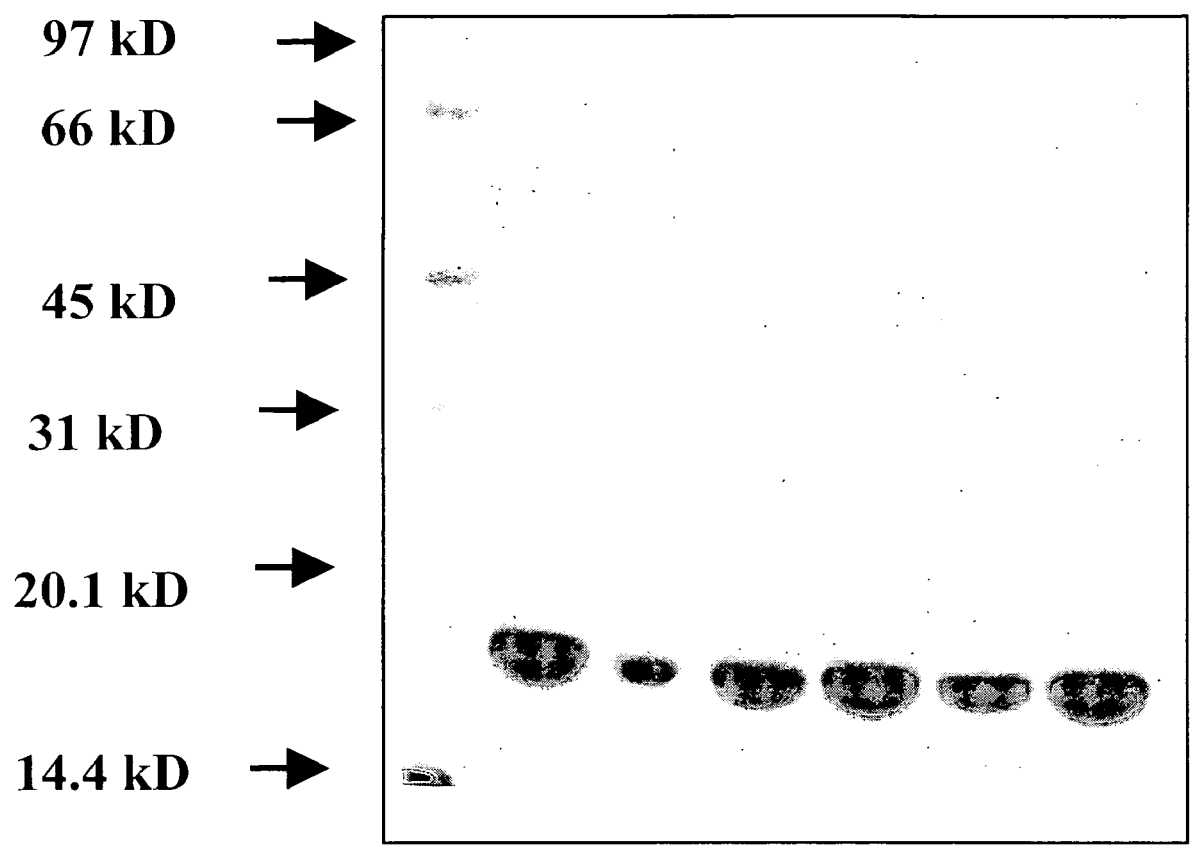

FIG. 4: SDS-PAGE profiles of the purified proteins. All the lipases were purified by the procedures given in examples: Low Molecular weight marker, Lane 1; wild-type lipase, Lane 2; Gene sequence 2, Lane 3; Gene sequence 3, Lane 4; Gene sequence 4, Lane 5; Gene sequence 5, Lane 6; Gene sequence 6, Lane 7.

Figure 5:
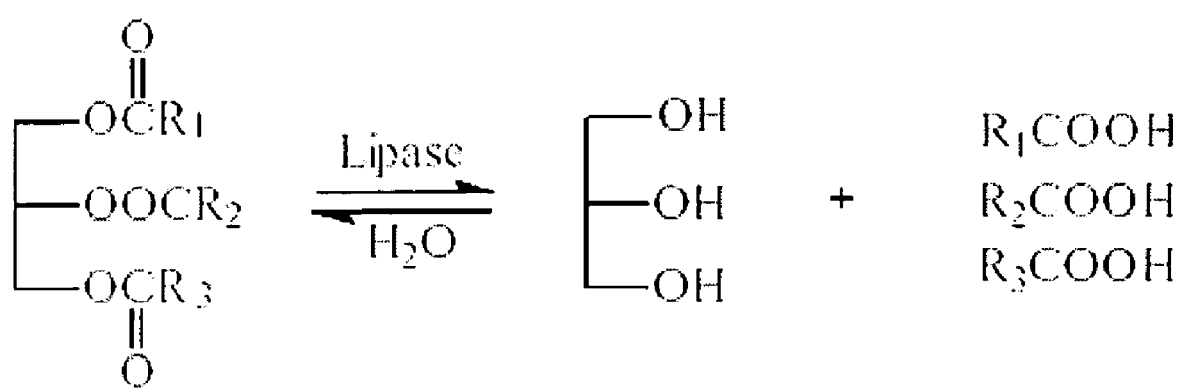

FIG. 5: Hydrolysis of a triglyceride catalyzed by a lipase. The schematic of the action of lipase on triglycerides is given. Lipase acts on the ester bonds and produces free fatty acids and glycerol.

Figure 6:
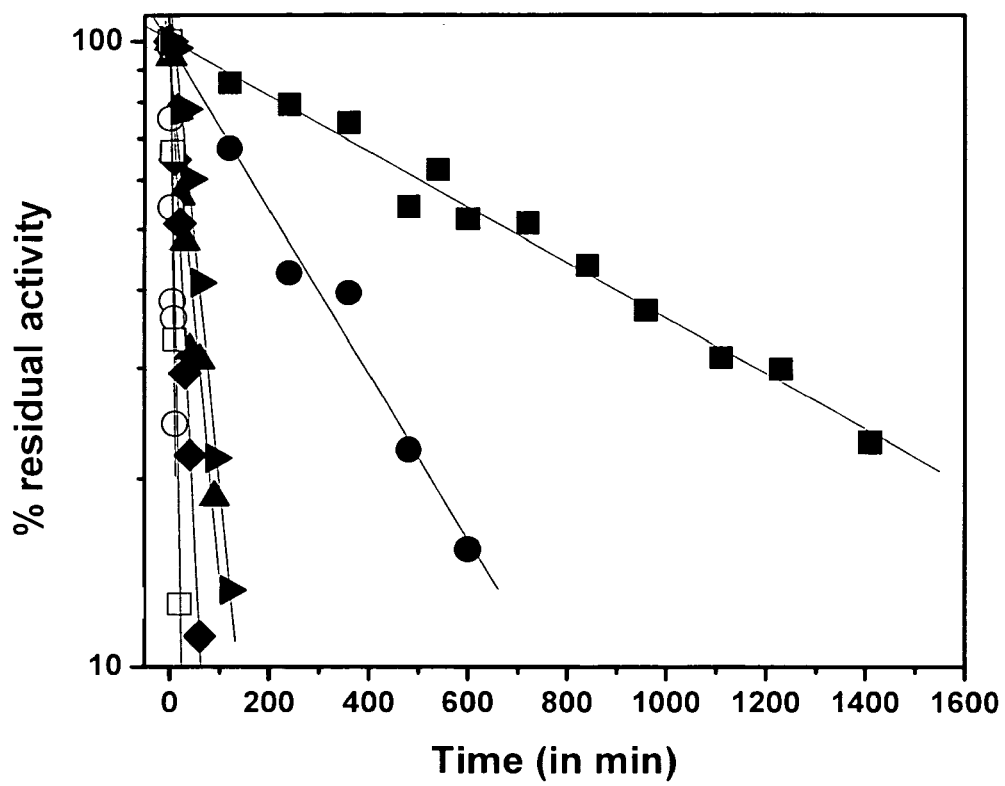

FIG. 6: Residual activity of various mutants and the wild type at a various times on exposure to a temperature of 55 C. The substrate used is PNPA. Wild type and the mutant enzymes were incubated at 55 C fro various lengths of time and the activity was estimated on cooling the enzyme on ice for few minutes. The activity was estimated at room temperature. The activity was expressed as the rate of hydrolysis of PNPA. Hydrolysis of PNPA was monitored as increase in absortion at 410 nm in a spectrometer.

Figure 7:
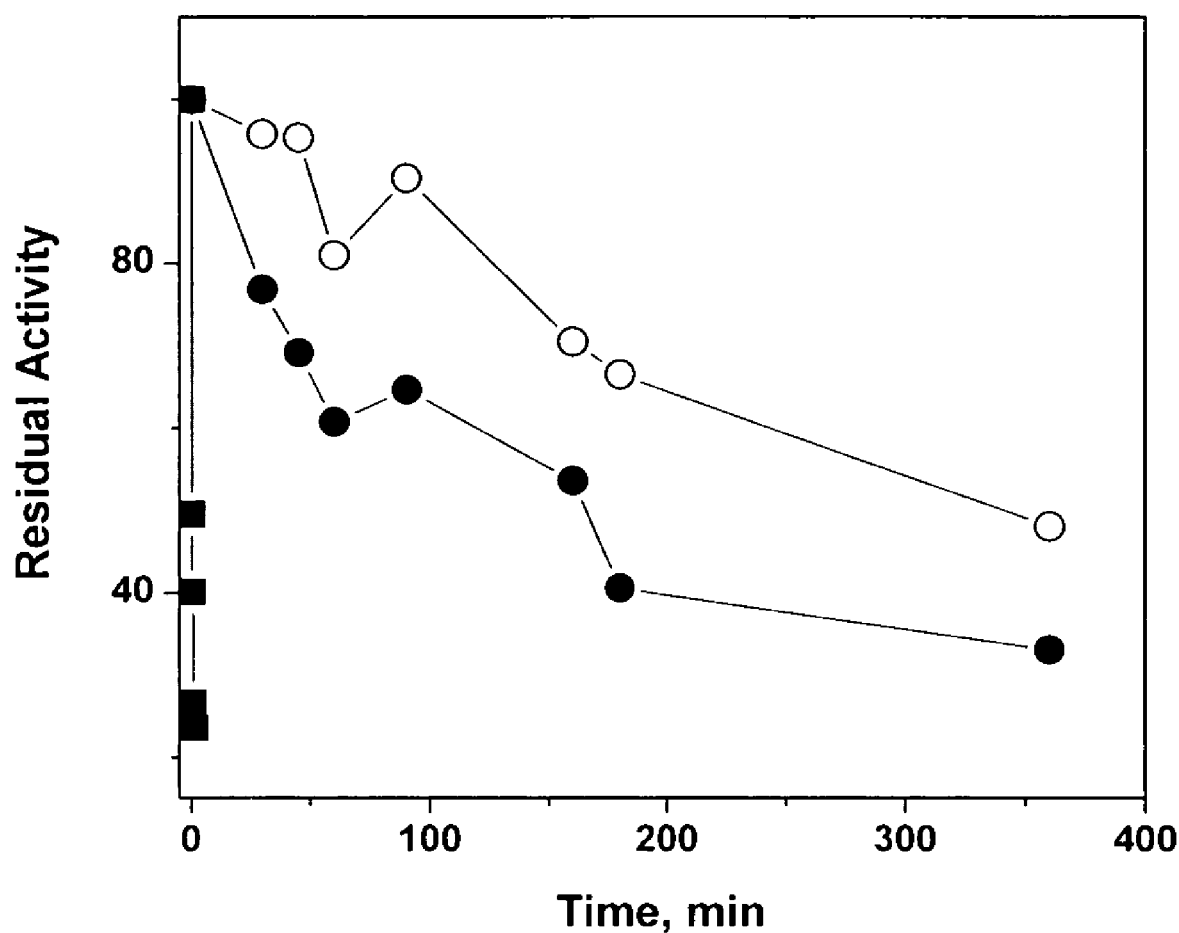

FIG. 7: Residual activity of various mutants and the wild type at various times on exposure to temperature of 50 C. The substrate used is olive oil. Substrate olive oil was emulsified using gum Arabic. The rate of hydrolysis of olive oil was monitored in a pH stat (Metrohm 718 pH Titrino) as the rate of addition of 0.1 nm sodium hydroxide per min. Hydrolysis of olive oil decrease the pH which was neutralized by sodium hydroxide.

Figure 8:
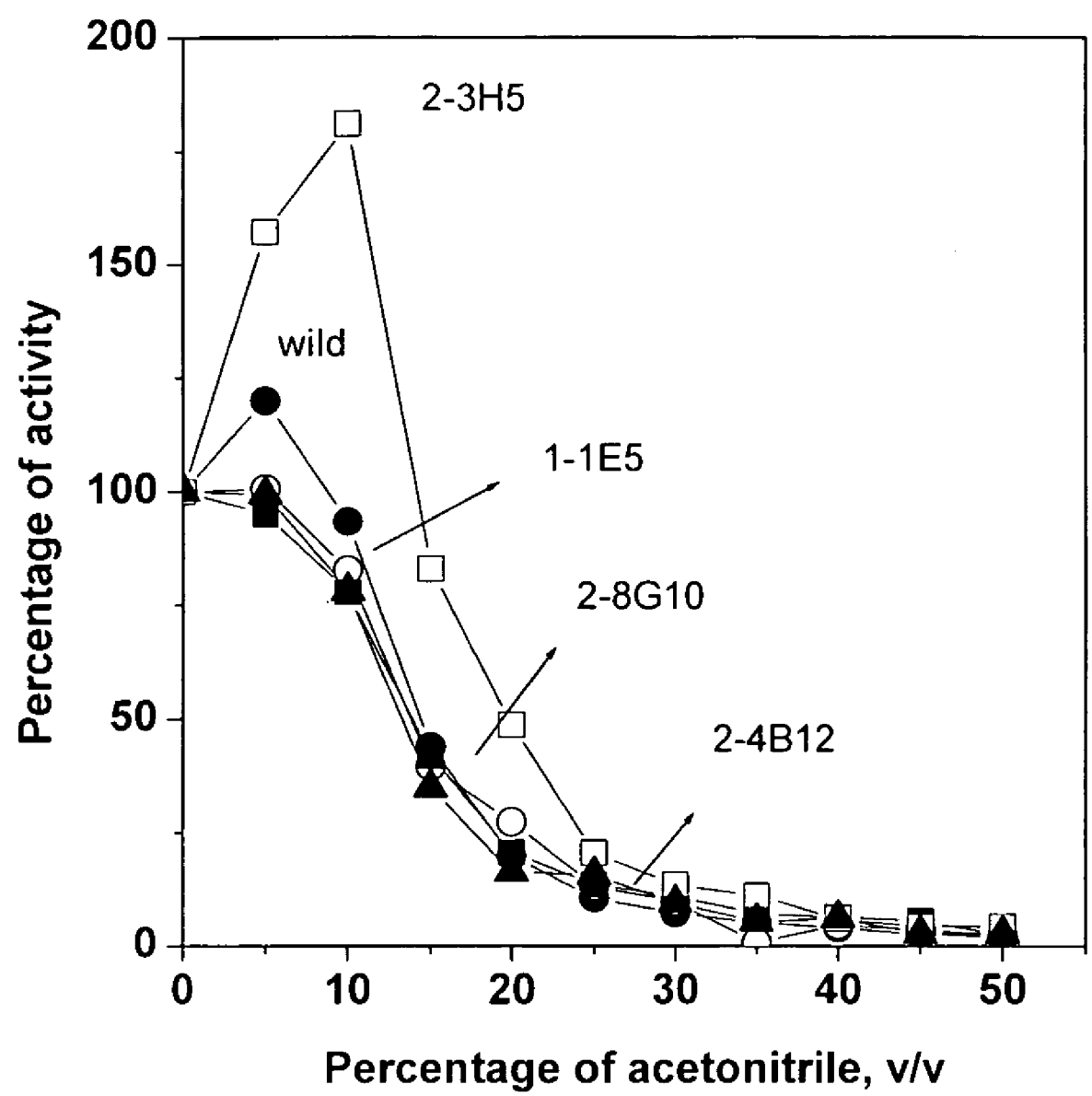

FIG. 8: Activity of lipase and its mutants in the presence of acetonitrile at various concentrations in water. Wild type and mutant enzymes were incubated in a medium containing various amounts of acetonitrile. The remaining activity at a fixed incubation time of 30 min was estimated using PNPA as substrate.

Figure 9:
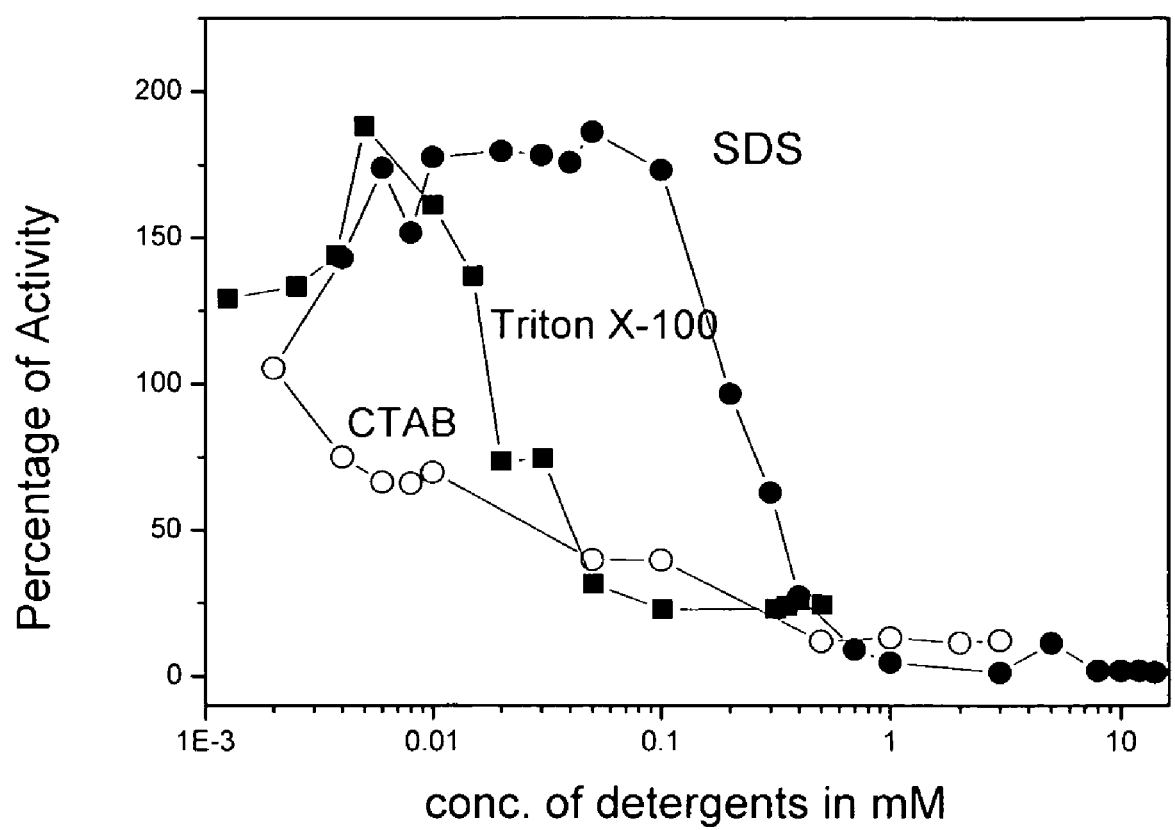

FIG. 9: Wild type lipase was incubated in the presence of various amounts of three different detergents for 30 min and the activity was assayed after 30 min. The three detergents were neutral detergent Triton X-100, anionic detergent, sodium dodecyl sulphate and cationic detergent, cetyl trimethylammonium bromide.

SUMMARY OF THE INVENTION

The present invention relates to novel gene variants of lipase enzyme as developed through site directed muatgenesis. These gene variants are highly thermostable, resistant against strong organic solvents and can tolerate high pH. The thermostability of the developed gene variants was as high 200 fold in the temperature range of 50 to 90°. The developed gene variants due to high thermostability, specific activity and tolerance due to high pH have application in household detergents and laundry industry.

DESCRIPTION OF THE INVENTION

In the present invention a method of directed evolution were applied to the lipase gene (Seq ID No.23) to isolate protein variants of the original sequence which possess increased thermostable properties. The methodology relies initially on the ability to create random variations in the original gene sequence and express the corresponding proteins in the bacteria, *E. coli*. The produced variants of the original sequence would have altered sequence, hence altered properties. The variants, at a proteins level, would be tested for their thermostability and those sequences which demonstrate improved thermostability would be subjected to the next round of random mutagenesis and screening. Thus by sequential accumulation of the mutants and subsequent pooling of the mutations the thermostability of lipase was improved by 200-fold at high temperature. High temperature range includes temperature ranges from 50-90 C.

The method according to the present invention includes four steps in generating the variant lipases and their characterization to obtain thermostable lipases. In the first of the methods variation in the primary sequence of the lipase gene were generated by error prone PCR methods. The adapted protocols are similar to several published protocols. In addition many of the different protocols such as random priming, ITCHY etc could also be applied for generation of variance in the gene sequence (Lutz and Benkovic, 2000; Shao et al., 1998). In the second step of the invention, the mutant sequences are cloned into an expression vector and the protein expressed in the culture lysates. The expressed proteins are screened for their ability to withstand higher temperature was tested in a large population using medium-throughput methods. In the third step of the invention the promising variants were pooled by a family shuffling procedures according to the method of Stemmer (1994) and further tested for thermostability. In addition to the shuffling procedures selective changes in the primary sequence were also incorporated by standard molecular biology procedures. In the fourth step of the invention the positive sequences were over-expressed in large cultures and the proteins are purified by the published procedures according to Dartois et al (1992). The purified proteins were tested for their thermostability.

The screening procedures of the lipase variants for increased thermostability involve ability to hydrolyse chromogenic substrate esters based on p-nitrophenyl group. Natural substrates of lipase are triglycerides, which are not convenient to design a simple medium trough put assays wherein the source of enzyme is over-expressed lipase in a cell lysate (Besson et al., 2000). P-nitrophenyl esters of fatty acids are convenient and the activity of lipase represents the activity of lipase on triglycerides. Long chain esters of p-nitrophenyl, especially p-nitrophenyl oleate, are well stilted for this purpose. Detergent solubilized PNPO demonstrates negligible back ground hydrolysis and well suited for lipase present in cell lysate. The strong yellow color of very high extinction coefficient of hydrolysis product p-nitrophenyl can be estimated conveniently in a 96-well plates. Along with p-nitrophenyl esters, many other fluorogenic or chromogenic esters of fatty acids could be used for this purpose. As employed herein the term thermostability refers to the property of the enzymes, which retain their activity subsequent to exposure to higher temperatures. Enzymes lose their tertiary conformation on exposure to higher temperature due to the increased movement of the structural elements, which perturbs the functional structure of the protein. Typically proteins lose their activity at higher temperatures with time. The rate of this loss in activity, reflects in half life i.e., time required to lose half of the initial activity, is a convenient parameter to compare the thermostability of the protein (Jaenicke and Bohm, 1998). Activity, as defined here, corresponds to the catalytic activity represented by the term kcat/Km, where kcat is the rate of the product formation and Km is the apparent affinity constant of the substrate to the enzyme. Retaining the functional structure at elevated temperatures resides in the ability to form interactions within the protein that withstand high temperatures. The range of the temperature that is relevant for the present invention ranges from 35 to 90 C.

The naturally occurring lipase from *Bacillus lipase* has the amino acid sequence of 1-181 as given in the SEQ ID No.1. (See also SEQ ID No. 23 for corresponding gene sequence). It was discovered that the amino acid substitutions at positions 68, 71, 114, 120, 132, 144, 147 and 166 were found to be important for the thermostability of the lipase. In accordance with the present investigation, it was further discovered that the substitutions at positions 114, 132 and 166 are suited for increasing the stability of the proteins. Any of the innumerable combinations of substitutions possible at each of these positions with the other 19 amino acids would be favourable for the thermostability.

The specific substitutions of relevance for thermostability in lipase are given below.

| From | To | Position |
|------|----|----------|
| N    | V  | 166      |
| A    | D  | 132      |
| A    | V  | 68       |
| L    | P  | 114      |
| R    | S  | 147      |
| V    | A  | 144      |
| N    | D  | 120      |

Accordingly, the main embodiment of the present invention relates to the novel thermostable, organic solvent resistant and high pH tolerant lipase gene variants having SEQ ID No. 2 of molecular wt 19443 (See also SEQ ID No. 24 for corresponding gene sequence), SEQ ID No. 3 of molecular wt 19515 (See also SEQ ID No. 25 for corresponding gene sequence), SEQ ID No. 4 of molecular wt 19456.9 (See also SEQ ID No. 26 for corresponding gene sequence), SEQ ID No.5 of molecular wt. 19487 (See also SEQ ID No. 27 for corresponding gene sequence), and SEQ ID No.6 of molecular wt. 19470.9 (See also SEQ ID No. 28 for corresponding gene sequence).

Another embodiment of the present invention relates to an expression system for novel thermostable, organic solvent resistant and high pH tolerant lipase gene variants said expression system comprising of having SEQ ID No. 2 of molecular wt 19443 (See also SEQ ID No. 24 for corresponding gene sequence), SEQ ID No. 3 of molecular wt 19515 (See also SEQ ID No. 25 for corresponding gene sequence), SEQ ID No. 4 of molecular wt 19456.9 (See also SEQ ID No. 26 for corresponding gene sequence), SEQ ID No.5 of molecular wt. 19487 (See also SEQ ID No. 27 for corresponding gene sequence) and SEQ ID No.6 of molecular wt 19470.9 (See also SEQ ID No. 28 for corresponding gene sequence) present in the vector pJO290.

Still another embodiment of the present invention relates to the a method of preparing an expression system of novel thermostable, organic solvent resistant and high pH tolerant lipase gene variants having SEQ ID No. 2 of molecular wt 19443 (See also SEQ ID No. 24 for corresponding gene sequence), SEQ ID No. 3 of molecular wt 19515 (See also SEQ ID No. 25 for corresponding gene sequence), SEQ ID No. 4 of molecular wt 19456.9 (See also SEQ ID No. 26 for corresponding gene sequence), SEQ ID No.5 of molecular wt. 19487 (See also SEQ ID No. 27 for corresponding gene sequence) and SEQ ID No.6 of molecular wt 19470.9 (See also SEQ ID No. 28 for corresponding gene sequence), said method comprising the steps of:
  (a) isolating and purifying lipase gene from *Bacillus subtilis*,
  (b) cloning lipase gene isolated in step (a) in vector pJO290,
  (c) generating gene variants from lipase gene isolated in step (a) by random mutagensis and site-directed mutagenesis using forward primer JOF having SEQ ID No.13 and reverse primer JOR having SEQ ID No. 14,
  (d) cloning the gene variants obtained in step (c) in plamsid vector pJO290, and
  (e) ligating the cloned gene variants of step (d) in *E. coli* JM109.

Another embodiment of the present invention relates to the gene variants wherein gene variants are thermostable in the temperature range of about 45 to 95° C.

One more embodiment of the present invention relates to the gene variants wherein said gene variants are highly thermostable at the temperature in the range of about 55 to 90° C. Still another embodiment of the present invention relates to the $T_{1/2}$ value of novel gene variants wherein $T_{1/2}$ value is in the range of 6 to 685.

Yet another embodiment of the present invention relates to the $T_{1/2}$ value of novel gene variants as wherein $T_{1/2}$ value is in the range of 7 to 677.

Another embodiment of the present invention relates to Km value of gene variants wherein Km value is in the range of 0.50 to 2.5 mM.

Still another embodiment of the present invention relates to the Km value of novel gene variants wherein Km value is in the range of 0.63 to 1.96 mM.

One more embodiment of the present invention relates to $k_{cat}$ value of the novel gene variants wherein $k_{cat}$ value is in the range of $4.5 \times 10^{-2}$ to $8.5 \times 10^{-2}$ min$^{-1}$.

Still another embodiment of the present invention relates to the $k_{cat}$ value of novel gene variants wherein $k_{cat}$ value is in the range of $5 \times 10^{-2}$ to $8.1 \times 10^{-2}$ min$^{-1}$.

Yet another embodiment of the present invention relates to the $k_{cat}/K_m$ value of novel gene variants wherein $k_{cat}/K_m$ value is in the range of $4 \times 10^{-2}$ to $10 \times 10^{-2}$ min$^{-1}$.

Another embodiment of the present invention relates to the $k_{cat}/K_m$ value of novel gene variants wherein $k_{cat}/K_m$, value is in the range of $4.1 \times 10^{-2}$ to $9.7 \times 10^{-2}$ min$^{-1}$.

One more embodiment of the present invention relates to the resistance of novel gene in organic solvents wherein organic solvents are selected from group of acetonitrile, isopropanol, dimethyl sulfoxide and dimethyl formide.

Still another embodiment of the present invention relates to the organic solvent used wherein organic solvent used is acetonitrile.

One more embodiment of the present invention relates to the residual activity of the gene variants wherein gene variants have residual activity in the range of 25 to 100% in presence of acetonitrile.

Another embodiment of the present invention relates to the residual activity of the gene variants wherein gene variants have residual activity in the range of 28.7 to 85.5% in presence of acetonitrile.

Still another embodiment of the present invention relates to the gene variants wherein the gene variants have inherent ability to withstand high pH in the range of 9 to 13; ability to withstand damaging surfactants and enzymes comprising groups of linear alkyl benzene sulfon ates, proteases and compounds thereof.

One more embodiment of the present invention relates to the to the gene variants wherein the gene variants have inherent ability to withstand high pH in the range of 10 to 11; ability to withstand damaging surfactants and enzymes comprising groups of linear alkyl benzene sulfonates, proteases and compounds thereof.

The following examples are given by way of illustration of the present invention and therefore should not be construed to limit the scope of the present invention.

EXAMPLES

Example 1

Purification of Lipase from *Bacillus subtilis*

Purification of the lipase was performed from *E. coli* cells expressing the lipase in an appropriate vector. The purification essentially involves passing the cell lysate in phenyl-sepharose column followed by a Mono-S column. Lipase is an aggregated prone protein, care especially keeping protein concentration below 5 mg/ml, was taken to avoid aggregation of the protein. The purification of the lipase was carried out essentially as described earlier[32] with minor modifications. Lipase from culture filterates of *Bacillus* strain or from the *E. coli* lysates was processed similarly. For purification of the wild type and mutant proteins from *E. coli* the lipA gene or the mutant genes are cloned into pET21b). For this, the gene corresponding to the full length, mature protein was amplified with primers PrNdeI (forward primer) (5'-CCAT-GATTACGCATATGGCTGAACACAA-3')(SEQ ID No. 15) and JOF. The forward primer had an engineered NdeI site. The forward primer also introduced a start codon at the start of the lipase gene in the form of the ATG sequence that is part of the NdeI recognition sequence. This would introduce a methionine in the N-terminus of the mature protein, expressed in *E. coli*, just before the N-terminal alanine that occurs in the protein purified from the culture supernatant of *B. subtilis*. The wild type protein as well as the mutants were amplified, digested with NdeI and BamHI and ligated with pET-21b digested with NdeI and BamHI. The ligation mix was transformed into *E. coli* DH5α and the positives were selected by plasmid minipreps and restriction digestions (FIG. 1 and FIG. 2).

Protein was purified from *E. coli* BL21 (DE3) cells. Cells containing the appropriate plasmid were grown till mid-log phase before inducing with 0.5 mM IPTG. Cells were harvested 2.5 hours after induction by centrifuging at 15,000 rpm at 4° C. for 20 min. The pellet was washed with STE and resuspended in 1×TE containing 0.3 mg/ml lysozyme. The suspension was incubated oil ice for 30 min before lysing the cells by sonication. Sonication was carried out by keeping the cells on ice. Short pulses of half-minute duration were applied and 1 min cooling time was allowed between pulses. The sonicated cells were centrifuged at 20,000 rpm at 4° C. The supernatant was loaded on a phenyl sepharose column. The remaining steps were done as described in chapter 2. The purified proteins were stored in −70° C. till further use.

*B. subtilis* BCL1051 was grown aerobically for 16-18 hrs at 37° C. in 21 Erlenmeyer flasks, each containing 500 ml of medium of the following composition: 2.4% yeast extract, 1.2% tryptone, 0.4% gum Arabic, 0.4% glycerol, 0.017 M KH$_2$PO$_4$, 0.072 M K$_2$HPO$_4$, 50 mg/ml kanamycin sulfate. The culture medium was inoculated at 1% from 10 ml precultures. After harvesting the cells by centrifugation at 6000 rpm for 30 min, the Culture supernatant was pumped at a flow rate of 30 ml/hr onto a Phenyl Sepharose Fast Flow High sub column (Pharmacia) (20 ml column volume per 11 culture) equilibrated with 100 mM potassium phosphate, pH 8.0. The column was washed at a flow rate of 50 ml/hr first with 10 mM potassium phosphate, pH 8.0 and then with 30% ethylene glycol in 10 mM potassium phosphate, pH 8.0. Elution was performed at a flow rate of 50 ml/hr with 80% ethylene glycol in 10 mM potassium phosphate, pH 8.0. 2 ml fractions were collected and the fractions containing protein (detected by absorbance at 280 nm) were checked for enzyme activity. The active fractions were pooled and dialyzed against 2 mM glycine-NaOH, pH 10.0. The dialyzed protein was diluted 1:1 with 50 mM Bicine-NaOH, pH 8.5 (buffer A) and loaded onto a MonoS HR5/5 (Pharmacia) column, pre-equilibrated with buffer A, using a Superloop (Pharmacia) on a FPLC (Pharmacia) system. The protein-bound-column was washed thoroughly with the buffer A to remove unbound proteins. The protein was eluted using a linear gradient with buffer A to buffer B (50 mM Bicine-NaOH, pH 8.5, 1 M NaCl). The enzyme eluted around 300 mM NaCl as a single peak. The active fractions eluted from the MonoS column were dialyzed overnight against 2 mM glycine, pH 10.0 and concentrated using an Amicon concentrator fitted with a YM10 membrane (10 kD cutoff). Purity of the protein was checked on a 12% SDS-PAGE gel containing 5 M urea (Lessuisse et al, 1993). The protein was >95% pure on a Coomassie stained gel (See FIG. 4).

Example 2

Assay of Lipase

Lipase belongs to a class of enzymes known as interfacially active enzymes. These enzymes have very little activity on the substrate monomers but their activity increases dramatically on insoluble substrate such as emulsified triglycerides, monolayers etc. This property makes lipases dissimilar to other enzymes which act on soluble substrate monomers. Triglycerides, natural substrates of lipase are not very convenient to set up simple chromogenic assays. Activity of pure lipases, sometimes, can be monitored by detecting the pH changes using pH-sensitive dyes. However, such assays yield complications when the enzyme source is a lysate and when there are other processes that may alter the pH. P-nitrophenyl esters are most convenient to monitor the activity. Short chain ester, p-nitrophenyl acetate and long chain ester, p-nitrophenyl oleate (PNPO), were synthesized by routine synthetic methods (given below). PNPO is a insoluble ester, was used in our assays using triton X-100 as a solubilizing agent. Triton X-100: PNPO co-micelles showed low back ground hydrolysis and were also stable at elevated temperatures. 96-well plate assays for screening the variants of lipase, though very useful to screen large number of samples, quantitates the activity approximately. All positives obtained in 96-well screens were confirmed in a tube assays, where the number of samples are less and more accurate specific activity calculations could be made. Synthesis of chromogenic substrates for lipase assays.

The following chromogenic substrates were synthesized for lipase assays:

1) p-nitrophenyl oleate
2) p-nitrophenyl stearate
3) p-nitrophenyl caprylate

The fatty acid, N,N'-methyltetrayl biscyclohexamine (dicyclohexylcarbodiimide, DCC), N,N'-dimethylamino pyridine (DMAP), and p-nitrophenol were taken in mole ratios of 1:1:1:2. The fatty acid was taken in a round bottom flask containing 20 ml of dry DCM and a few ml of chloroform. The mixture was stirred for two minutes followed by addition of DCC. A white precipitate was formed. This was followed by the addition of DMAP. Subsequent addition of p-nitrophenol led to the formation of a yellow precipitate. The reaction vessel was flushed with nitrogen and stirred for 5 hours. The progress of the reaction was monitored by thin layer chromatography. After completion of the reaction, the DCM was evaporated to dryness and the ester was purified by column chromatography (silica gel column, elution with petroleum ether-acetone). The purity and identity of the product was confirmed by $^1$H-NMR spectroscopy.

Example 3

Lipase assay in 96-well microtitre plates): The colonies obtained from the cloning of the PCR product generated by error-prone PCR were patched on another similar plate and simultaneously inoculated in separate wells of a microtitre plate containing 200 µl 2XYT containing 25 µg/ml chloramphenicol and 0.2% glucose. The cells were grown for 24 hours in the microtitre plate with continuous shaking at 200 rpm. After 24 hrs, 5 µl culture from each well was taken and added to the corresponding well another microtitre plate containing 200 µl 2XYT supplemented with 25 µg/ml chloramphenicol. After 3 hours of growth the cultures were induced with 1 mM IPTG. After 3 more hours 25 µl of culture was taken from every well into the corresponding wells of two fresh microtitre plates containing 25 µl phosphate buffer pH 7.0. One of the plates was exposed to high temperature for 20 min, cooled on ice for 15 min and then allowed to come to room temperature. The other plate was kept at room temperature. 25 pl of the PNPO-Triton X-100 substrate solution prepared as described above was added to each well. The plates were incubated at 37° C. and absorbance at 405 nm was recorded in an ELISA reader at definite time intervals. The clones showing less than 20% of the activity of the wild-type protein (or the parent from which it is generated) were removed from further consideration. The residual activity for each clone after exposure to high temperature was calculated. The clones showing highest residual activity were chosen for the next level of screening.

Lipase assails in tubes: The colonies that showed highest residual activity in the microtire plate level screen were grown for 12 hours in 5 ml 2XYT medium 25 µg/ml chloramphenicol and 0.2% glucose. 10 ml of 2XYT containing 25 µg/ml chloramphenicol and 0.2% glucose was inoculated with 100 µl of the overnight grown culture. After 2.5 hours growth, the cultures were induced with 1.5 mM IPTG and were harvested after another 2.5 hours. The cell pellet was washed with STE and resuspended in 1 ml 0.05 M potassium phosphate buffer pH 7.2. The cell suspension was sonicated with a Branson sonicator with four pulses of 30 sec and 1 min cooling time in between the pulses. The tubes were kept on ice during sonication and cooling of the samples. The sonicated samples were centrifuged at 15,000 rpm for 45 min and the supernatant was used for the assays. The supernatant was divided into four 250 µl aliquots. Three of the aliquots were exposed to higher temperatures and the fourth was kept on ice. The tubes were exposed to high temperatures for 20 min, chilled on ice, centrifuged at 4° C. at 15,000 rpm and then allowed to come to room temperature before assaying for enzymatic activity. The lipase activity in the cell lysates was determined at room temperature in sodium phosphate buffer pH 7.2 by using p-nitrophenyl oleate as substrate. The enzymatic activity was measured by following the change of absorbance at 405 nm with time. Lysates of cells that do not contain the lipase gene but otherwise processed in the same way as mentioned above, were used to determine the background hydrolysis of p-nitrophenyl oleate in *E. coli* cell lysate. The background hydrolysis values were subtracted from the enzymatic activity value. The total protein in the cell lysates was determined by Lowry's method and was used to normalize the activity.

Example 4

Half-lives of Thermal Inactivation

Exposing the enzymes to higher temperatures and then assaying the activity at room temperature normally assess thermostability of enzymes. At higher temperature the protein denatures and irreversible unfolds. Thermostable enzymes possess additional stabilizing interactions which would make them less susceptible for heat denaturations. The activity remaining is residual activity, which decrease both with increase in temperature or with increase in time at a given temperature. Heat treatment of the purified proteins was carried out in a programmable thermal cycler (Gene-Amp PCR system 9700) in 0.2 ml thin-walled PCR tubes to allow precise temperature control of the samples. The proteins were taken at a concentration of 0.05 mg/ml in 0.05 M sodium phosphate buffer, pH 7.0. 25 µl of protein samples were taken in each tube. The proteins were heated for the required time, cooled at 4° C. for 20 min, centrifuged and equilibrated at room temperature before assaying for enzymatic activity. 20 µl of the heat-treated protein sample was added to 1 ml 0.05 M sodium phosphate, pH 7.2 containing 2 mM p-nitrophenyl acetate. Enzymatic activity was measured at 25° C. by monitoring the rate of increase in absorbance at 405 nm. Typically, inactivation was followed until >80% of the activity was lost. Plots of log(residual activity) versus time were linear. Inactivation rate constants ($k_{inact}$) were obtained from the slope and half-lives were calculated as $t_{1/2}=\log 2/k_{inact}$. The half lives of various mutants obtained were presented in figure (FIG. 6 and Table 1) where the residual activities were measured using PNPA as substrate. The enzyme mutants were exposed to 55 C. In FIG. 7 data obtained with residual activities with three mutants using olive oil as a substrate was presented. The activities were measured using pH stat equipment. This data demonstrates that the enhancement seen with mutants was independent of the substrate and nature of the assay.

Preparation of Substrate Stocks

Appropriate amounts of the insoluble p-nitrophenyl ester and Triton X-100 were weighed out in a glass vial and mixed with a magnetic stirrer till the ester completely dissolved in Triton X-100. Buffer was added slowly while stirring to prepare a 2× stock solution containing 0.4 mM p-nitrophenyl ester and 40 mM Triton X-100. Substrate solutions prepared in this way were optically clear. 100× substrate stocks of the water-soluble p-nitrophenyl acetate were made in acetone and 2 mM p-nitrophenyl acetate was used for each reaction. The reactions were carried out in absence of Triton X-100 and all the measurements to determine kinetic parameters were done with this reaction system.

Example 5

Assay with Olive Oil (Diagrammatic Sketch of Breakdown of Fats/Detergents by Lipases, FIG. 5)

Assay with the olive oil is performed pH stat equipment. All lipases subsequent to thir activity reduce th pH off the reaction medium by releasing a proton. The decrease in pH could be neutralized by addition of known amounts of alkali. The rate of additon of alkali would represent the activity of the lipase. We have prepared the lipase substrate by mixing gum Arabic (0.5%), olive oil and CaCl2. The mixture was sonicated in a bath till we obtain a uniform emulsion. We have used. 10 ml of the substrate for each assay. At the beginning of the asay the pH of the substrate was brought to 8.4 by addition of alkali. The reaction was started with the addition of 10 microlitres of 1 mg/ml enzyme solution. The rate of reaction was calculated from the slopes of amount of alkali vs. time curves). 1 N NaOH was sued as alkali.

Example 6

Methods of Generation of Variations in the Lipase Genes

The sequence of LipA, whose product is lipase gene of interest in this invention, from *Bacillus subtilis* was published. In *Bacillus* LipA gene product is secreted into the culture medium owing to the presence of a signal sequence at the N-terminal of the sequence, which aids in its transport out of the cell. Molecular biology of *Bacillus* species has been well studied and it is a Gram-positive strain. For routine molecular biology techniques such as transformation, cloning, expression etc. *Bacillus* sp. is less suited compared to *E. coli* (Sambrook et al., 1989; Hoch et al., 1993). The main difficulty is in transforming the *Bacillus* sp with the plasmids. The efficiency is lower by several orders of magnitude compared to *E. coli*. Further, the observed efficiencies are only detectable with electroporation, which is a harsher method. In *E. coli* the transformation efficiency is higher and reproducible and the choice of plasmids is wide. To perform various gene manipulations, *E. coli* was used.

The clone pLipA containing the complete lipA gene in pBR322 plasmid was a kind gift from Dr Frens Pierce (FIG. 1). The lipase gene along with the region coding for the signal sequence was amplified with primers ForI (forward

TABLE 1

| SEQ ID No. 6 | | SEQ ID No. 5 | | SEQ ID No. 1 | | SEQ ID No. 3 | | SEQ ID No. 4 | | SEQ ID No. 2 | |
|---|---|---|---|---|---|---|---|---|---|---|---|
| Time, min | Activity | Time, min | Activity | Time, min | Activity | Time, min | Activity | Time, min | Activity | Time, min | Activity |
| 0 | 100 | 0 | 100 | 0 | 100 | 0 | 100 | 0 | 100 | 0 | 100 |
| 120 | 85.88 | 120 | 67.52 | 0.5 | 97.65 | 10 | 64.75 | 5 | 66.7466 | 2.5 | 94.5 |
| 240 | 79.2133 | 240 | 42.635 | 1.25 | 75.3 | 20 | 51.1233 | 10 | 7 | 7.833 | 77 |
| 360 | 3 | 360 | 39.58 | 2.5 | 54.25 | 30 | 3 | 20 | 33.3333 | 15 | 77.6 |
| 480 | 74.115 | 480 | 22.205 | 5 | 38.4 | 40 | 29.45 | 30 | 3 | 20 | 56.54 |
| 540 | 54.415 | 540 | — | 7.5 | 36.02 | 60 | 21.81 |  | 12.5933 | 30 | 47.9 |
| 600 | 62.354 | 600 | 15.425 | 10 | 24.4 |  | 11.1766 |  | 3 | 40 | 32.03 |
| 720 | 51.94 |  |  |  |  |  | 7 |  | 5.54333 | 60 | 30.9 |
| 840 | 51.18 |  |  |  |  |  |  |  |  | 90 | 18.66 |
| 960 | 43.82 |  |  |  |  |  |  |  |  |  |  |
| 1110 | 37.055 |  |  |  |  |  |  |  |  |  |  |
| 1230 | 31.1735 |  |  |  |  |  |  |  |  |  |  |
| 1410 | 29.85 |  |  |  |  |  |  |  |  |  |  |
|  | 22.79 |  |  |  |  |  |  |  |  |  |  | primer) (5'-GGAGGATCATATGAAATTTGTAAAAA-3') (SEQ ID No. 16) and Rev1 (reverse primer) (5'-CCCGG-GATCCATTGTCCGTTACC-3')(SEQ ID No. 17). The primers contained engineered NdeI and BamHI sites respectively. The ATG of the NdeI site in ForI coincided with the natural start codon of the lipase and the BamHI site was beyond the natural stop codon. The amplified product was digested with NdeI and BamHI and cloned into the NdeI-BamHI sites of the plasmid pET-21b yielding the plasmid pET-lipwt (FIG. 2). The lipase gene coding for the mature protein was amplified from pET-lipwt by using primers PREcoRI (forward primer) (5'-CGTCAGCGAATTCCGCT-GAACACAT-3')(SEQ ID No. 18) and PRBamHI (reverse primer) (5'-GCGGGAAGGATCCGAATTCGAGCT-3') (SEQ ID No. 19). The primers had an engineered EcoRI and BamHI site respectively. The amplified product was cleaved by EcoRI and BamHI and cloned into the EcoRI-BamHI sites of the plasmid pJO290. This construct (pJO290lip) was used for screening thermostable mutants (FIG. 3). The E. coli strain JM109 was used for all the screening steps and all media contained 0.2% glucose unless otherwise mentioned. This system was chosen because it allows low-level, controlled and inducible expression of the gene product in E. coli, which is necessary to prevent the reported toxicity of the protein to E. coli and to prevent complications from in vivo insolubility of this highly hydrophobic and aggregation-prone protein.

Methods of Random Mutagenesis

The critical step in the invention is in the ability to create variations in the gene. The variation generated should be "sufficient" to yield functional variants. Enzymes have evolved over millions of years of evolution and in the process the enzymes may have tested and avoided deleterious mutations and also tested and incorporated beneficial mutations. It is also believed that most of the gene mutations would be silent i.e., they do not bring about a change in amino acid sequence. In random mutagenesis protocols, it is essential to obtain variations in the gene sequence that result in non-silent mutations and excess of variations, wherein the gene product would be non-functional or may not form. Error-prone PCR based mutagenesis protocols need to be optimized to obtain sufficient variation in the activity of the lipase. The success of the directed evolution protocols strongly depends on the control of this variable. The protocols used in the present example were modifications of the published procedures.

The lipase gene was mutagenised by error-prone PCR (Cadwell and Joyce, 1992). Primers JOF (5'-CGC-CAGGGTTTTCCCAGTCACGAC-3')(SEQ ID No. 20) and JOR (5'-TGACACAGGAAACAGCTATGAC-3')(SEQ ID No. 21) flank the gene beyond the EcoRI and BamHI sites present on the plasmid. Error-prone PCR was carried out in a 100 μl reaction volume containing 20 femtomoles of the plasmid pJO290-lip, 50 pmoles each of primers JOF and JOR, 100 mM Tris.Cl (pH 8.3 at 25° C.), 500 mM KCl, 0.1% gelatin (w/v), 7 mM MgCl$_2$, 0.25 mM MnCl$_2$, 1 mM each of dTTP and dCTP, 0.2 mM each of dATP and dCTP and 5 units Taq DNA polymerase. After an initial denaturation of 3 min at 94° C., the following steps were repeated for 30 cycles in a thermal cycler: 1 min at 94° C., 1 min at 45° C. and 1 min at 72° C. The amplified product was precipitated with ethanol, eluted from a 1% agarose gel and digested with EcoRI and BamHI. The digested product was again eluted from a 1% agarose gel and ligated with pJO290 digested with EcoRI and BamHI. The ligation mix was transformed into E. coli JM109 and selection was done on LB-agar supplemented with 25 μg/ml chloramphenicol and 0.2% glucose.

Site-directed Mutagenesis

Site directed mutagenesis was carried out on the lipase gene cloned in pET-21b by a modified PCR technique (Chen and Arnold, 1991). For each substitution an oligonucleotide containing the desired mutation was used as the primer (mismatch primer) to initiate chain extension between the 5' and 3' PCR primers. In the first PCR, the mismatch primer and the 3' primer were used to generate a DNA fragment containing the new base substitution. The fragment was separated from the template and primers by agarose gel electrophoresis, purified and used as the new 3' primer in a second PCR with the 5' primer to generate full length product, which was cloned into pET-21b for expression of the mutant protein.

Example 7

Recombination of the Clones Obtained in Generation 2

The mutant Gene sequence 27 was created from the clone 2-8G10 and wt by using the unique restriction site HaeII at position 910 of the lipase gene. The genes coding for the two proteins were amplified by PCR using the T7 promoter and terminator primers. The PCR products were purified by gel extraction and digested with HaeII and NdeI. The upper and lower bands correspond to the C-terminal and N-terminal regions of the protein, respectively. The upper band from clone 2-8G10 and the lower one from the wild-type protein were eluted. The higher molecular weight fragment was digested with BamHI and purified. A three point ligation containing the NdeI-HaeII fragment (from the wt), the HaeII-BamHI fragment (from 2-8G10) and pET-21b cut with NdeI and HaeII was set up, the ligation mix transformed into DH5α and the positives selected. The sequence of the gene was confirmed by DNA sequencing.

The mutant Gene sequence 28 (triple mutant) was created by site-directed mutagenesis on the Gene sequence 5 template using the mutagenic primer PROLF: 5'-GGC AAG GCG CCT CCG GGA ACA GAT-3' to incorporate a codon change CTT→CCT that led to L114P change in the amino acid sequence. The sequences of all the genes were confirmed by automated DNA sequencing.

Example 8

Enzyme Kinetics

All kinetic measurements were made using a thermostatted spectrophotometer using the water-soluble substrate p-nitrophenyl acetate. Initial rates of hydrolysis of p-nitrophenyl acetate at various concentrations were determined at 25° C. in sodium phosphate buffer pH 7.2. The values for $K_M$ and $k_{cat}$ were derived from the corresponding Lineweaver-Burke plots. The kinetic parameters obtained with wild type and the mutants was presented in Table 2.

TABLE 2

| | Kinetic parameters for the wild-type lipase and the thermostable mutants | | | |
|---|---|---|---|---|
| Clone | $K_m$, mM | $k_{cat} \times 10^{-2}$ min$^{-1}$ | $k_{cat}/K_m \times 10^{-2}$, mM$^{-1}$ · min$^{-1}$ | $T_{1/2}$, min (55° C., pH 7.0) |
| Control (SEQ ID No. 1) | 0.97 | 5.2 | 5.4 | 2.5 |
| SEQ ID No. 2 | 1.03 | 5.0 | 4.85 | 25.4 |
| SEQ ID No. 3 | 0.69 | 5.5 | 8.0 | 18.9 |

TABLE 2-continued

Kinetic parameters for the wild-type lipase and the thermostable mutants

| Clone | $K_m$, mM | $k_{cat} \times 10^{-2}$, min$^{-1}$ | $k_{cat}/K_m \times 10^{-2}$, mM$^{-1} \cdot$ min$^{-1}$ | $T_{1/2}$, min (55° C., pH 7.0) |
|---|---|---|---|---|
| SEQ ID No. 4 | 0.63 | 6.1 | 9.7 | 7.0 |
| SEQ ID No. 5 | 1.22 | 6.8 | 5.6 | 228.0 |
| SEQ ID No. 8 | 1.45 | 7.5 | 5.2 | 46.1 |
| SEQ ID No. 6 | 1.96 | 8.1 | 4.1 | 677.0 |

Example 9

Activity of Lipase and its Mutants in the Presence of Organic Solvents

The activity of the lipase and its mutants was checked in the presence of various solvents. The organic solvents tested were acetonitrile, isopropanol, dimethyl sulfoxide and dimethyl formamide. The activity assay was performed using PNPA as a substrate. The substrate (2 mM) was dissolved in various percents (v/v) of the organic solvent in buffer (50 mM pH 8.0) and the reaction was started with the addition of lipase at a concentration of 0.246 mg/ml. The activity was monitored as n increase in absorption at 410 nm and the specific activity was calculated using the initial slopes of the curve. In FIG. 8 and Table 3 the data obtained with acetonitrile is presented.

TABLE 3

| | Residual activity (as Percent of control) at 20% Acetonitrile (v/v) |
|---|---|
| Control (SEQ ID No. 1) | 22 |
| SEQ ID No. 2 | 28.7 |
| SEQ ID No. 3 | 61.6 |
| SEQ ID No. 4 | 85.5 |
| SEQ ID No. 7 | 52.3 |

Example 10

Wild type lipase or control lipase activity in presence of various of detergents. (FIG. 9) Having thus described exemplary embodiments of the present invention, it should be noted by those skilled in the art that the disclosures herein are exemplary only and that various other alternations, adaptations and modifications may be made within the scope of the present invention. Accordingly, the present invention is not limited to the specific embodiments as illustrated herein.

The preceding examples demonstrate the usefulness of the present invention in generating, identifying and isolating lipases which have improved stability and/or ester hydrolysis activity at higher temperature in organic media relative to the natural enzyme.

REFERENCES

1. Karsherkoff, A. and Ladenstein, R. TIBS (2001) 26, 550-556
2. Kumar, S, Tsai, C-J and Nussinov, R. (2000) Protein Engg. 13: 179-191.
3. Lehmann, B. et. al. (2000) Protein Engg. 13: 49-57.
4. Jaenicke, R. and Bohm, G. (1998) Curr. Opin. Struct. Biol. 8, 738-748.
5. Vogt, G., Woell, S. and Argos, P. (1997a) J. Mol. Biol. 269, 631-643.
6. Vogt, G., Woell, S. and Argos, P. (1997b) Folding Design, 1, S40-S46.
7. Ladenstein, R. and Antranikian, G. (1998) Adv. Biochem. Eng. Biotechnol. 61, 37-85.
8. Reetz M T, Zonta A, Simpelkamp J. (1995) Angew Chem, Int Ed Engl 34, 301-303.
9. Plou, F. J. and Ballesteros A. TIBS (1999) 17, 304-306
10. Argos, P., Rossmann, M. G., Grau, U., Zuber, H., Frank, G., and Tratschin, J. D. (1979) Biochemistry, 18, 5698-5703.
11. Arnold, F. (1999) Engineering and Science No. 1/2, 41-50.
12. Stemmer, W. P. C. (1994) Nature (London) 370: 389-39
13. Ostermeier M, Shim J H, Benkovic S J. (1999) Nat. Biotechnol., 17, 1205-9.
14. Woolley, P and Petersen, S. B. (Ed.) Lipase: their structure, biochemistry and application (1994) Cambridge University Press.
15. Jaeger, K-E., Dijkstra, B. W. and Reetz, M. T. (1999) Annu. Rev. Microbiol. 53:315-351.
16. Schmid, R. D. and Verger, R. (1998) Angew. Chem. Int. Ed. Engl. 37, 1608-1633.
17. Jaeger K E, Reetz T M. (1998) Trends Biotechnol. 16, 396-403.
18. Wang, L. J., Kong, X. D., Zhang, H. Y., Wang, X. P, and Zhang J. Biochem Biophys Res Commun Sep 276:346-349.
19. Rubin, B. and Dennis, E. A. (1997) Lipases Part A: Biotechnology, Methods Enzymol. 286, pp 563, Academic press, San diego.
20. Kazlauskas R J, Bornscheuer U T. Biotransformations with lipases. In: Rehm H J, Pihler G, Stadler A, Kelly P J W, editors. Biotechnology. vol. 8. New York: VCH, 1998. pp. 37-192.
21. Gerritse G, Hommes R W, and Quax W J. (1998) J Appl Environ Microbiol, 64, 2644-51.
22. Bycroft, A. L. and Byng, G. S. (1992) European patent application 0468102A1
23. Kennedy, M. B. and Lennarz, W. J. (1979) J. Biol. Chem. 254, 1080-1089.
24. Dartois, V., Baulard, A., Schanck, K. and Colson, C. (1992) Biochim. Biophys. Acta 1131: 253-260.
25. Lesuisse, E., Schanck, K. and Colson, C. (1993) Eur. J. Biochem. 216, 155-160.
26. Eggert, T., Pencreac'h, G., Douchet, I., Verger, R. and Jaeger, K.-E. (2000) Eur. J. Biochem. 267, 6459-6469.
27. Arpigny, J. L and Jaeger, K.-E. (1999) Biochem J. 343, 177-183.
28. Pouderoyen, G., Eggert, T., Jaeger, K. E. and Djikstra, B. W. (2001) J Mol Biol. 309: 215-226.
29. Lutz, S. and benkovic, S. J. (2000) Cur. Opi. Biotech. 11, 319-324.
30. Shao Z, Zhao H, Giver L, and Arnold F H (1998) Nucleic Acids Res. 26, 681-683.
31. Beisson, F., Alim Tiss, Riviere, C. and Verger, R. (2000) Eur. J. lipid Sci. Tech 133-153
32. Sambrook, J., Fritsch, E. F. and Maniatis, T. (1989) Molecular cloning: a laboratory manual (2$^{nd}$ Edition) Cold spring Harbor laboratory Press
33. Hoch, J. A., Sonenshein, A. L. and Losick, R. (1993) Bacillus subtislis and other gram positive bacteria, ASM.

We claim:

1. A thermostable, organic solvent resistant and high pH tolerant lipase variant having an amino acid sequence selected from the group consisting of SEQ ID No. 2, SEQ ID No. 3, SEQ ID No. 4, SEQ ID No.5, SEQ ID No.6, SEQ ID No. 7 and SEQ ID No. 8.

2. The lipase variant as claimed in claim 1, wherein said lipase variant is thermostable in the temperature range of about 45 to 95° C.

3. The lipase variant as claimed in claim 2, wherein said lipase variant is highly thermostable at the temperature in the range of about 55 to 90° C.

4. The lipase variant as claimed in claim 1, wherein said lipase variant has a $T_{1/2}$ value in the range of 6 to 685.

5. The lipase variant as claimed in claim 1, wherein said lipase variant has a $T_{1/2}$ value in the range of 7 to 677.

6. The lipase variant as claimed in claim 1, wherein said lipase variant has a Km value in the range of 0.50 to 2.5 mM.

7. The lipase variant as claimed in claim 1, wherein said lipase variant has a Km value in the range of 0.63 to 1.96 mM.

8. The lipase variant as claimed in claim 1, wherein said lipase variant has a $k_{cat}$ value in the range of $4.5 \times 10^{-2}$ to $8.5 \times 10^{-2}$ min$^{-1}$.

9. The lipase variant as claimed in claim 1, wherein said lipase variant has a $k_{cat}$ value in the range of $5 \times 10^{-2}$ to $8.1 \times 10^{-2}$ min$^{-1}$.

10. The lipase variant as claimed in claim 1, wherein said lipase variant has a $k_{cat}/K_m$ value in the range of $4 \times 10^{-2}$ to $10 \times 10^{-2}$ min$^{-1}$.

11. The lipase variant as claimed in claim 1, wherein said lipase variant has a $k_{cat}/K_m$ value in the range of $4.1 \times 10^{-2}$ to $9.7 \times 10^{-2}$ min$^{-1}$.

12. The lipase variant as claimed in claim 1, wherein said lipase variant is resistant to an organic solvent selected from group of acetonitrile, isopropanol, dimethyl sulfoxide and dimethyl formide.

13. The lipase variant as claimed in claim 12, wherein the organic solvent is acetonitrile.

14. The lipase variant as claimed in claim 1, wherein said lipase variant has residual activity in the range of 25 to 100% in presence of acetonitrile.

15. The lipase variant as claimed in claim 1, wherein said lipase variant has residual activity in the range of 28.7 to 85.5% in presence of acetonitrile.

16. The lipase variant as claimed in claim 1, wherein the lipase variant has inherent ability to withstand a pH in the range of 9 to 13 and ability to withstand a damaging surfactant.

17. The lipase variant as claimed in claim 1 having the amino acid sequence of SEQ ID No. 3.

18. The lipase variant as claimed in claim 1 having the amino acid sequence of SEQ ID No. 4.

19. The lipase variant as claimed in claim 1 having the amino acid sequence of SEQ ID No. 5.

20. The lipase variant as claimed in claim 1 having the amino acid sequence of SEQ ID No. 6.

21. The lipase variant as claimed in claim 1 having the amino acid sequence of SEQ ID No. 7.

22. The lipase variant as claimed in claim 1 having the amino acid sequence of SEQ ID No. 8.

23. The lipase variant of claim 16, wherein the damaging surfactant is a linear alkyl benzene sulfonate.

24. The lipase variant of claim 1, wherein the variant has inherent ability to withstand a pH in the range of 9 to 13 and ability to withstand a damaging enzyme.

25. The lipase variant of claim 24, wherein the damaging enzyme is a protease.

* * * * *

SEQUENCE LISTING

<160> NUMBER OF SEQ ID NOS: 12

<210> SEQ ID NO 1
<211> LENGTH: 181
<212> TYPE: PRT
<213> ORGANISM: Bacillus subtilis
<220> FEATURE:
<221> NAME/KEY: AMINO ACIDS
<222> LOCATION: (1)..(181)
<223> OTHER INFORMATION: enzyme sequence

<400> SEQUENCE: 1

```
Met Ala Glu His Asn Pro Val Val Met Val His Gly Ile Gly Gly Ala
1               5                   10                  15

Ser Phe Asn Phe Ala Gly Ile Lys Ser Tyr Leu Val Ser Gln Gly Trp
            20                  25                  30

Ser Arg Asp Lys Leu Tyr Ala Val Asp Phe Trp Asp Lys Thr Gly Thr
        35                  40                  45

Asn Tyr Asn Asn Gly Pro Val Leu Ser Arg Phe Val Gln Lys Val Leu
    50                  55                  60

Asp Glu Thr Gly Ala Lys Lys Val Asp Ile Val Ala His Ser Met Gly
65                  70                  75                  80

Gly Ala Asn Thr Leu Tyr Tyr Ile Lys Asn Leu Asp Gly Gly Asn Lys
                85                  90                  95

Val Ala Asn Val Val Thr Leu Gly Gly Ala Asn Arg Leu Thr Thr Gly
            100                 105                 110

Lys Ala Leu Pro Gly Thr Asp Pro Asn Gln Lys Ile Leu Tyr Thr Ser
        115                 120                 125

Ile Tyr Ser Ser Ala Asp Met Ile Val Met Asn Tyr Leu Ser Arg Leu
    130                 135                 140

Asp Gly Ala Arg Asn Val Gln Ile His Gly Gly His Ile Gly Leu Leu
145                 150                 155                 160

Tyr Ser Ser Gln Val Asn Ser Leu Ile Lys Glu Gly Leu Asn Gly Gly
                165                 170                 175

Gly Gln Asn Thr Asn
            180
```

<210> SEQ ID NO 2
<211> LENGTH: 181
<212> TYPE: PRT
<213> ORGANISM: Bacillus subtilis
<220> FEATURE:
<221> NAME/KEY: Amino acid
<222> LOCATION: (1)..(181)
<223> OTHER INFORMATION: Protein sequence

<400> SEQUENCE: 2

```
Met Ala Glu His Asn Pro Val Val Met Val His Gly Ile Gly Gly Ala
1               5                   10                  15

Ser Phe Asn Phe Ala Gly Ile Lys Ser Tyr Leu Val Ser Gln Gly Trp
            20                  25                  30

Ser Arg Asp Lys Leu Tyr Ala Val Asp Phe Trp Asp Lys Thr Gly Thr
        35                  40                  45

Asn Tyr Asn Asn Gly Pro Val Leu Ser Arg Phe Val Gln Lys Val Leu
    50                  55                  60

Asp Glu Thr Gly Ala Lys Lys Val Asp Ile Val Ala His Ser Met Gly
65                  70                  75                  80
```

```
Gly Ala Asn Thr Leu Tyr Tyr Ile Lys Asn Leu Asp Gly Gly Asn Lys
                85                  90                  95

Val Ala Asn Val Val Thr Leu Gly Gly Ala Asn Arg Leu Thr Thr Gly
            100                 105                 110

Lys Ala Leu Pro Gly Thr Asp Pro Asn Gln Lys Ile Leu Tyr Thr Ser
            115                 120                 125

Ile Tyr Ser Ser Ala Asp Met Ile Val Met Asn Tyr Leu Ser Arg Leu
            130                 135                 140

Asp Gly Ala Arg Asn Val Gln Ile His Gly His Ile Gly Leu Leu
145                 150                 155                 160

Tyr Ser Ser Gln Val Tyr Ser Leu Ile Lys Glu Gly Leu Asn Gly Gly
                165                 170                 175

Gly Gln Asn Thr Asn
            180

<210> SEQ ID NO 3
<211> LENGTH: 181
<212> TYPE: PRT
<213> ORGANISM: Bacillus subtilis
<220> FEATURE:
<221> NAME/KEY: Amino acid
<222> LOCATION: (1)..(181)
<223> OTHER INFORMATION: Protein sequence

<400> SEQUENCE: 3

Met Ala Glu His Asn Pro Val Val Met Val His Gly Ile Gly Gly Ala
1               5                   10                  15

Ser Phe Asn Phe Ala Gly Ile Lys Ser Tyr Leu Val Ser Gln Gly Trp
                20                  25                  30

Ser Arg Asp Lys Leu Tyr Ala Val Asp Phe Trp Asp Lys Thr Gly Thr
            35                  40                  45

Asn Tyr Asn Asn Gly Pro Val Leu Ser Arg Phe Val Gln Lys Val Leu
        50                  55                  60

Asp Glu Thr Gly Val Lys Lys Val Asp Ile Val Ala His Ser Met Gly
65                  70                  75                  80

Gly Ala Asn Thr Leu Tyr Tyr Ile Lys Asn Leu Asp Gly Gly Asn Lys
                85                  90                  95

Val Ala Asn Val Val Thr Leu Gly Gly Ala Asn Arg Leu Thr Thr Gly
            100                 105                 110

Lys Ala Leu Pro Gly Thr Asp Pro Asn Gln Lys Ile Leu Tyr Thr Ser
            115                 120                 125

Ile Tyr Ser Ser Asp Asp Met Ile Val Met Asn Tyr Leu Ser Arg Leu
            130                 135                 140

Asp Gly Ala Arg Asn Val Gln Ile His Gly His Ile Gly Leu Leu
145                 150                 155                 160

Tyr Ser Ser Gln Val Tyr Ser Leu Ile Lys Glu Gly Leu Asn Gly Gly
                165                 170                 175

Gly Gln Asn Thr Asn
            180

<210> SEQ ID NO 4
<211> LENGTH: 181
<212> TYPE: PRT
<213> ORGANISM: Bacillus subtilis
<220> FEATURE:
<221> NAME/KEY: Amino acid
<222> LOCATION: (1)..(181)
<223> OTHER INFORMATION: Protein Sequence
```

<400> SEQUENCE: 4

```
Met Ala Glu His Asn Pro Val Val Met Val His Gly Ile Gly Gly Ala
1               5                   10                  15

Ser Phe Asn Phe Ala Gly Ile Lys Ser Tyr Leu Val Ser Gln Gly Trp
            20                  25                  30

Ser Arg Asp Lys Leu Tyr Ala Val Asp Phe Trp Asp Lys Thr Gly Thr
        35                  40                  45

Asn Tyr Asn Asn Gly Pro Val Leu Ser Arg Phe Val Gln Lys Val Leu
    50                  55                  60

Asp Glu Thr Gly Thr Lys Lys Val Asp Ile Val Ala His Ser Met Gly
65                  70                  75                  80

Gly Ala Asn Thr Leu Tyr Tyr Ile Lys Asn Leu Asp Gly Gly Asn Lys
                85                  90                  95

Val Ala Asn Val Val Thr Leu Gly Gly Ala Asn Arg Leu Thr Thr Gly
            100                 105                 110

Lys Ala Pro Pro Gly Thr Asp Pro Asn Gln Lys Ile Leu Tyr Thr Ser
        115                 120                 125

Ile Tyr Ser Ser Ala Asp Met Ile Val Met Asn Tyr Leu Ser Arg Leu
    130                 135                 140

Asp Gly Ala Arg Asn Val Gln Ile His Gly Gly His Ile Gly Leu Leu
145                 150                 155                 160

Tyr Ser Ser Gln Val Tyr Ser Leu Ile Lys Glu Gly Leu Asn Gly Gly
                165                 170                 175

Gly Gln Asn Thr Asn
                180
```

<210> SEQ ID NO 5
<211> LENGTH: 181
<212> TYPE: PRT
<213> ORGANISM: Bacillus subtilis
<220> FEATURE:
<221> NAME/KEY: Amino acid
<222> LOCATION: (1)..(181)
<223> OTHER INFORMATION: Protein Sequence

<400> SEQUENCE: 5

```
Met Ala Glu His Asn Pro Val Val Met Val His Gly Ile Gly Gly Ala
1               5                   10                  15

Ser Phe Asn Phe Ala Gly Ile Lys Ser Tyr Leu Val Ser Gln Gly Trp
            20                  25                  30

Ser Arg Asp Lys Leu Tyr Ala Val Asp Phe Trp Asp Lys Thr Gly Thr
        35                  40                  45

Asn Tyr Asn Asn Gly Pro Val Leu Ser Arg Phe Val Gln Lys Val Leu
    50                  55                  60

Asp Glu Thr Gly Ala Lys Lys Val Asp Ile Val Ala His Ser Met Gly
65                  70                  75                  80

Gly Ala Asn Thr Leu Tyr Tyr Ile Lys Asn Leu Asp Gly Gly Asn Lys
                85                  90                  95

Val Ala Asn Val Val Thr Leu Gly Gly Ala Asn Arg Leu Thr Thr Gly
            100                 105                 110

Lys Ala Leu Pro Gly Thr Asp Pro Asn Gln Lys Ile Leu Tyr Thr Ser
        115                 120                 125

Ile Tyr Ser Ser Asp Asp Met Ile Val Met Asn Tyr Leu Ser Arg Leu
    130                 135                 140

Asp Gly Ala Arg Asn Val Gln Ile His Gly Gly His Ile Gly Leu Leu
145                 150                 155                 160
```

Tyr Ser Ser Gln Val Tyr Ser Leu Ile Lys Glu Gly Leu Asn Gly Gly
                165                 170                 175

Gly Gln Asn Thr Asn
            180

<210> SEQ ID NO 6
<211> LENGTH: 181
<212> TYPE: PRT
<213> ORGANISM: Bacillus subtilis
<220> FEATURE:
<221> NAME/KEY: Amino acid
<222> LOCATION: (1)..(181)
<223> OTHER INFORMATION: Protein sequence

<400> SEQUENCE: 6

Met Ala Glu His Asn Pro Val Val Met Val His Gly Ile Gly Gly Ala
1               5                   10                  15

Ser Phe Asn Phe Ala Gly Ile Lys Ser Tyr Leu Val Ser Gln Gly Trp
            20                  25                  30

Ser Arg Asp Lys Leu Tyr Ala Val Asp Phe Trp Asp Lys Thr Gly Thr
        35                  40                  45

Asn Tyr Asn Asn Gly Pro Val Leu Ser Arg Phe Val Gln Lys Val Leu
    50                  55                  60

Asp Glu Thr Gly Ala Lys Lys Val Asp Ile Val Ala His Ser Met Gly
65                  70                  75                  80

Gly Ala Asn Thr Leu Tyr Tyr Ile Lys Asn Leu Asp Gly Gly Asn Lys
                85                  90                  95

Val Ala Asn Val Val Thr Leu Gly Gly Ala Asn Arg Leu Thr Thr Gly
            100                 105                 110

Lys Ala Pro Pro Gly Thr Asp Pro Asn Gln Lys Ile Leu Tyr Thr Ser
        115                 120                 125

Ile Tyr Ser Ser Asp Asp Met Ile Val Met Asn Tyr Leu Ser Arg Leu
    130                 135                 140

Asp Gly Ala Arg Asn Val Gln Ile His Gly Gly His Ile Gly Leu Leu
145                 150                 155                 160

Tyr Ser Ser Gln Val Tyr Ser Leu Ile Lys Glu Gly Leu Asn Gly Gly
                165                 170                 175

Gly Gln Asn Thr Asn
            180

<210> SEQ ID NO 7
<211> LENGTH: 181
<212> TYPE: PRT
<213> ORGANISM: Bacillus subtilis
<220> FEATURE:
<221> NAME/KEY: Amino acid
<222> LOCATION: (1)..(181)
<223> OTHER INFORMATION: Protein sequence

<400> SEQUENCE: 7

Met Ala Glu His Asn Pro Val Val Met Val His Gly Ile Gly Gly Ala
1               5                   10                  15

Ser Phe Asn Phe Ala Gly Ile Lys Ser Tyr Leu Val Ser Gln Gly Trp
            20                  25                  30

Ser Arg Asp Lys Leu Tyr Ala Val Asp Phe Trp Asp Lys Thr Gly Thr
        35                  40                  45

Asn Tyr Asn Asn Gly Pro Val Leu Ser Arg Phe Val Gln Lys Val Leu
    50                  55                  60

-continued

```
Asp Glu Thr Gly Ala Lys Lys Val Asp Ile Val Ala His Ser Met Gly
 65                  70                  75                  80

Gly Ala Asn Thr Leu Tyr Tyr Ile Lys Asn Leu Asp Gly Gly Asn Lys
                 85                  90                  95

Val Ala Asn Val Val Thr Leu Gly Gly Ala Asn Arg Leu Thr Thr Gly
            100                 105                 110

Lys Ala Leu Pro Gly Thr Asp Pro Asn Gln Lys Ile Leu Tyr Thr Ser
        115                 120                 125

Ile Tyr Ser Ser Ala Asp Met Ile Val Met Asn Tyr Leu Ser Arg Leu
    130                 135                 140

Asp Gly Ala Ser Asn Val Gln Ile His Gly His Ile Gly Leu Leu
145                 150                 155                 160

Tyr Ser Ser Gln Val Tyr Ser Leu Ile Lys Glu Gly Leu Asn Gly Gly
                165                 170                 175

Gly Gln Asn Thr Asn
            180
```

<210> SEQ ID NO 8
<211> LENGTH: 181
<212> TYPE: PRT
<213> ORGANISM: Bacillus subtilis
<220> FEATURE:
<221> NAME/KEY: Amino acid
<222> LOCATION: (1)..(181)
<223> OTHER INFORMATION: Protein sequence

<400> SEQUENCE: 8

```
Met Ala Glu His Asn Pro Val Val Met Val His Gly Ile Gly Gly Ala
 1               5                  10                  15

Ser Phe Asn Phe Ala Gly Ile Lys Ser Tyr Leu Val Ser Gln Gly Trp
                20                  25                  30

Ser Arg Asp Lys Leu Tyr Ala Val Asp Phe Trp Asp Lys Thr Gly Thr
            35                  40                  45

Asn Tyr Asn Asn Gly Pro Val Leu Ser Arg Phe Val Gln Lys Val Leu
 50                  55                  60

Asp Glu Thr Gly Ala Lys Lys Val Asp Ile Val Ala His Ser Met Gly
 65                  70                  75                  80

Gly Ala Asn Thr Leu Tyr Tyr Ile Lys Asn Leu Asp Gly Gly Asn Lys
                 85                  90                  95

Val Ala Asn Val Val Thr Leu Gly Gly Ala Asn Arg Leu Thr Thr Gly
            100                 105                 110

Lys Ala Pro Pro Gly Thr Asp Pro Asn Gln Lys Ile Leu Tyr Thr Ser
        115                 120                 125

Ile Tyr Ser Ser Ala Asp Met Ile Val Met Asn Tyr Leu Ser Arg Leu
    130                 135                 140

Asp Gly Ala Arg Asn Val Gln Ile His Gly His Ile Gly Leu Leu
145                 150                 155                 160

Tyr Ser Ser Gln Val Tyr Ser Leu Ile Lys Glu Gly Leu Asn Gly Gly
                165                 170                 175

Gly Gln Asn Thr Asn
            180
```

<210> SEQ ID NO 9
<211> LENGTH: 181
<212> TYPE: PRT
<213> ORGANISM: Bacillus subtilis
<220> FEATURE:
<221> NAME/KEY: Amino acid
<222> LOCATION: (1)..(181)
<223> OTHER INFORMATION: Portein Sequence

<400> SEQUENCE: 9

```
Met Ala Glu His Asn Pro Val Val Met Val His Gly Ile Gly Gly Ala
1               5                   10                  15

Ser Phe Asn Phe Ala Gly Ile Lys Ser Tyr Leu Val Ser Gln Gly Trp
            20                  25                  30

Ser Arg Asp Lys Leu Tyr Ala Val Asp Phe Trp Asp Lys Thr Gly Thr
        35                  40                  45

Asn Tyr Asn Asn Gly Pro Val Leu Ser Arg Phe Val Gln Lys Val Leu
    50                  55                  60

Asp Glu Thr Gly Ala Lys Lys Ala Asp Ile Val Ala His Ser Met Gly
65                  70                  75                  80

Gly Ala Asn Thr Leu Tyr Tyr Ile Lys Asn Leu Asp Gly Gly Asn Lys
                85                  90                  95

Val Ala Asn Val Val Thr Leu Gly Gly Ala Asn Arg Leu Thr Thr Gly
            100                 105                 110

Lys Ala Leu Pro Gly Thr Asp Pro Asn Gln Lys Ile Leu Tyr Thr Ser
        115                 120                 125

Ile Tyr Ser Ser Ala Asp Met Ile Val Met Asn Tyr Leu Ser Arg Leu
    130                 135                 140

Asp Gly Ala Arg Asn Val Gln Ile His Gly His Ile Gly Leu Leu
145                 150                 155                 160

Tyr Ser Ser Gln Val Tyr Ser Leu Ile Lys Glu Gly Leu Asn Gly Gly
                165                 170                 175

Gly Gln Asn Thr Asn
            180
```

<210> SEQ ID NO 10
<211> LENGTH: 181
<212> TYPE: PRT
<213> ORGANISM: Bacillus subtilis
<220> FEATURE:
<221> NAME/KEY: Amino acid
<222> LOCATION: (1)..(181)
<223> OTHER INFORMATION: Protein Sequence

<400> SEQUENCE: 10

```
Met Ala Glu His Asn Pro Val Val Met Val His Gly Ile Gly Gly Ala
1               5                   10                  15

Ser Phe Asn Phe Ala Gly Ile Lys Ser Tyr Leu Val Ser Gln Gly Trp
            20                  25                  30

Ser Arg Asp Lys Leu Tyr Ala Val Asp Phe Trp Asp Lys Thr Gly Thr
        35                  40                  45

Asn Tyr Asn Asn Gly Pro Val Leu Ser Arg Phe Val Gln Lys Val Leu
    50                  55                  60

Asp Glu Thr Gly Ala Lys Lys Val Asp Ile Val Ala His Ser Met Gly
65                  70                  75                  80

Gly Ala Asn Thr Leu Tyr Tyr Ile Lys Asn Leu Asp Gly Gly Asn Lys
                85                  90                  95

Val Ala Asn Val Val Thr Leu Gly Gly Ala Asn Arg Leu Thr Thr Gly
            100                 105                 110

Lys Ala Leu Pro Gly Thr Asp Pro Asn Gln Lys Ile Leu Tyr Thr Ser
        115                 120                 125

Ile Tyr Ser Ser Ala Asp Met Ile Val Met Asn Tyr Leu Ser Arg Leu
    130                 135                 140
```

```
Val Gly Ala Arg Asn Val Gln Ile His Gly Gly His Ile Gly Leu Leu
145                 150                 155                 160

Tyr Ser Ser Gln Val Tyr Ser Leu Ile Lys Glu Gly Leu Asn Gly Gly
                165                 170                 175

Gly Gln Asn Thr Asn
            180

<210> SEQ ID NO 11
<211> LENGTH: 181
<212> TYPE: PRT
<213> ORGANISM: Bacillus subtilis
<220> FEATURE:
<221> NAME/KEY: Amino acid
<222> LOCATION: (1)..(181)
<223> OTHER INFORMATION: Protein sequence

<400> SEQUENCE: 11

Met Ala Glu His Asn Pro Val Val Met Val His Gly Ile Gly Gly Ala
1               5                   10                  15

Ser Phe Asn Phe Ala Gly Ile Lys Ser Tyr Leu Val Ser Gln Gly Trp
                20                  25                  30

Ser Arg Asp Lys Leu Tyr Ala Val Asp Phe Trp Asp Lys Thr Gly Thr
            35                  40                  45

Asn Tyr Asn Asn Gly Pro Val Leu Ser Arg Phe Val Gln Lys Val Leu
50                  55                  60

Asp Glu Thr Gly Val Lys Lys Val Asp Ile Val Ala His Ser Met Gly
65                  70                  75                  80

Gly Ala Asn Thr Leu Tyr Tyr Ile Lys Asn Leu Asp Gly Gly Asn Lys
                85                  90                  95

Val Ala Asn Val Val Thr Leu Gly Gly Ala Asn Arg Leu Thr Thr Gly
                100                 105                 110

Lys Ala Leu Pro Gly Thr Asp Pro Asn Gln Lys Ile Leu Tyr Thr Ser
            115                 120                 125

Ile Tyr Ser Ser Asp Asp Met Ile Val Met Asn Tyr Leu Ser Arg Leu
130                 135                 140

Asp Gly Ala Arg Asn Val Gln Ile His Gly Gly His Ile Gly Leu Leu
145                 150                 155                 160

Tyr Ser Ser Gln Val Tyr Ser Leu Ile Lys Glu Gly Leu Asn Gly Gly
                165                 170                 175

Gly Gln Asn Thr Asn
            180

<210> SEQ ID NO 12
<211> LENGTH: 181
<212> TYPE: PRT
<213> ORGANISM: Bacillus subtilis
<220> FEATURE:
<221> NAME/KEY: Amino acid
<222> LOCATION: (1)..(181)
<223> OTHER INFORMATION: Protein sequence
<220> FEATURE:
<221> NAME/KEY: Amino ]acid
<222> LOCATION: (1)..(181)
<223> OTHER INFORMATION: Protein sequence

<400> SEQUENCE: 12

Met Ala Glu His Asn Pro Val Val Met Val His Gly Ile Gly Gly Ala
1               5                   10                  15

Ser Phe Asn Phe Ala Gly Ile Lys Ser Tyr Leu Val Ser Gln Gly Trp
                20                  25                  30
```

```
Ser Arg Asp Lys Leu Tyr Ala Val Asp Phe Trp Asp Lys Thr Gly Thr
    35              40              45
Asn Tyr Asn Asn Gly Pro Val Leu Ser Arg Phe Val Gln Lys Val Leu
    50              55              60
Asp Glu Thr Gly Ala Lys Lys Val Asp Ile Val Ala His Ser Met Gly
65              70              75                      80
Gly Ala Asn Thr Leu Tyr Tyr Ile Lys Asn Leu Asp Gly Gly Asn Lys
                85              90                      95
Val Ala Asn Val Val Thr Leu Gly Gly Ala Asn Arg Leu Thr Thr Gly
            100             105             110
Lys Ala Pro Pro Gly Thr Asp Pro Asp Gln Lys Ile Leu Tyr Thr Ser
        115             120             125
Ile Tyr Ser Ser Asp Asp Met Ile Val Met Asn Tyr Leu Ser Arg Leu
    130             135             140
Asp Gly Ala Arg Asn Val Gln Ile His Gly Gly His Ile Gly Leu Leu
145             150             155             160
Tyr Ser Ser Gln Val Tyr Ser Leu Ile Lys Glu Gly Leu Asn Gly Gly
            165             170             175
Gly Gln Asn Thr Asn
            180
```